(12) United States Patent
Metz, Jr.

(10) Patent No.: US 8,008,340 B2
(45) Date of Patent: *Aug. 30, 2011

(54) 3-ARYLTHIOINDOLE-2-CARBOXAMIDE DERIVATIVES AND ANALOGS THEREOF AS INHIBITORS OF CASEIN KINASE I

(75) Inventor: William Arthur Metz, Jr., Bridgewater, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 640 days.

This patent is subject to a terminal disclaimer.

(21) Appl. No.: 11/675,230

(22) Filed: Feb. 15, 2007

(65) Prior Publication Data

US 2007/0142454 A1 Jun. 21, 2007

Related U.S. Application Data

(63) Continuation of application No. PCT/US2005/029306, filed on Aug. 19, 2005.

(60) Provisional application No. 60/603,348, filed on Aug. 19, 2004.

(51) Int. Cl.
- *A01N 43/38* (2006.01)
- *A61K 31/40* (2006.01)
- *C07D 209/04* (2006.01)

(52) U.S. Cl. ........................ 514/421; 514/414; 548/469
(58) Field of Classification Search .................. 514/421, 514/414; 548/469
See application file for complete search history.

(56) References Cited

U.S. PATENT DOCUMENTS 6,555,328 B1 4/2003 Keesler et al.

FOREIGN PATENT DOCUMENTS

| DE | 3705934 | 9/1988 |
|---|---|---|
| WO | WO 94/19321 | 9/1994 |
| WO | WO 03/078435 | 9/2003 |
| WO | WO 2004/014300 | 2/2004 |
| WO | WO 2005/061498 | 7/2005 |

OTHER PUBLICATIONS

Boschelli et al. "Inhibition of E-Selectin-,ICAM-1, and VCAM-1-Mediated Cell Adhesion by Benzo[b]thiphene, Benzofuran-, Indole-, and Naphthalene-2-carboxamides: Identification of PD 144795 as an Antiinflammatory Agent" J. Med. Chem., 1995, vol. 38, pp. 4597-4614.*

Hasegawa, M., et. al.,, Regulation of the Circadian Oscillator in *Xenopus* Retinal Photoreceptors by Protein Kinases Sensitive to the Stress-Activatived Protein Kinase Inhibitor, SB203580, The Journal of Biological Chemistry, vol. 279, No. 21 pp. 22738-22746 (2004).

* cited by examiner

*Primary Examiner* — Sreeni Padmanabhan
*Assistant Examiner* — Kendra D Carter
(74) *Attorney, Agent, or Firm* — Serena Farquharson-Torres; Balaram Gupta; Kelly Bender

(57) ABSTRACT

A method for inhibiting casein kinase I$\epsilon$ activity, comprising administering to said patient a therapeutically effective amount of a compound of formula I.

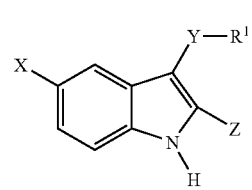

its stereoisomer, enantiomer, racemate, tautomer or pharmaceutically acceptable salt thereof.

12 Claims, No Drawings

3-ARYLTHIOINDOLE-2-CARBOXAMIDE DERIVATIVES AND ANALOGS THEREOF AS INHIBITORS OF CASEIN KINASE I

CROSS-REFERENCE TO RELATED APPLICATIONS

This application is a continuation of International Patent Application No. PCT/US2005/029306 filed on Aug. 19, 2005 which is incorporated herein by reference in its entirety which also claims the benefit of priority of U.S. Provisional Appln. Ser. No. 60/603,348 filed on Aug. 19, 2004

FIELD OF THE INVENTION

This invention relates generally to methods for the treatment and/or prevention of diseases and disorders associated with the central nervous system, more particularly, those involving compounds and compositions useful in the regulation of the human clock protein Period (hPER). More specifically, the present invention relates to a series of compounds and compositions that are inhibitors of human casein kinase Iε phosphorylation of the human clock protein Period (hPER) which are thereby useful as pharmaceutical agents. More specifically, the present invention comprises therapeutic methods for treating the afore-mentioned diseases using 3-arylthioindole-2-carboxamide derivatives and their analogs. More specifically, the present invention relates to the use of compositions comprising 3-arylthioindole-2-carboxamides and 5-substituted-3-arylthioindole-2-carboxamides and related analogs thereof as pharmaceutical agents in therapeutic applications of the central nervous system.

BACKGROUND OF THE INVENTION

Rhythmic variations in behavior are displayed by many organisms, ranging from single cells to man. When the rhythm persists under constant conditions, and has a period of about one day, depending little on temperature, the rhythm is called "circadian" (Konopka, R. J. and Benzer, S. (1971) Proc. Nat. Acad. Sci. USA 68, 2112-2116).

Circadian rhythms are generated by endogenous biological pacemakers (circadian clocks) and are present in most living organisms including humans, fungi, insects and bacteria (Dunlap, J. C. (1999) Cell 96, 271-290; Hastings, J. W. et al. Circadian Rhythms, The Physiology of Biological Timing. In: Prosser, C. L. ed. Neural and Integrative Animal Physiology, New York: Wiley-Liss (1991) 435-546; Allada, R. et al. (1998) Cell 93, 791-804; Kondo et al. (1994) Science 266, 1233-1236; Crosthwaite, S. K. et al. (1997) Science 276, 763-769; Shearman, L. P. et al. (1997) Neuron, 19, 1261-1269). Circadian rhythms are self-sustaining and constant even under conditions of total darkness, but can be synchronized (entrained) to a new day/night regime by environmental signals such as light and temperature cycles (Pittendrigh, C. S. (1993) Annu. Rev. Physiol., 55, 16-54; Takahashi, J. S. (1995) Annu. Rev. Neurosci. 18, 531-553; Albrecht, U. et al. (1997) Cell, 91, 1055-1064). Circadian clocks are essential for maintaining biological rhythms and regulate a variety of circadian behaviors such as daily fluctuations in behavior, food intake and the sleep/wake cycle, as well as physiological changes such as hormone secretion and fluctuations in body temperature (Hastings, M. (1997) Trends Neurosci. 20, 459-464; Reppert, S. M. and Weaver, D. R. (1997) Cell 89, 487-490).

Genetic and molecular studies in the fruit fly *Drosophila melanogaster* led to elucidation of some of the genes involved in circadian rhythmicity. These studies led to recognition of a pathway that is closely auto-regulated and comprised of a transcription/translation-based negative feed back loop (Dunlap, J. C. (1999) Cell, 96, 271-290; Dunlap, J. C. (1996) Annu. Rev. Genet. 30, 579-601; Hall, J. C. (1996) Neuron, 17, 799-802). The core elements of the circadian oscillator in *Drosophila* consists of two stimulatory proteins dCLOCK/dBMAL (CYCLE) and two inhibitory proteins dPERIOD (dPER) and dTIMELESS (dTIM). dCLOCK and dBMAL heterodimerize forming the transcription factor dCLOCK/dBMAL that promotes expression of two genes termed *Drosophila* Period (dper) and *Drosophila* Timeless (dtim). Ultimately the mRNAs from these genes are transcribed to afford the proteins dPER and dTIM, respectively. For several hours the protein products dPER and dTIM are synthesized and phosphorylated in the cytoplasm, reach a critical level, and form heterodimers that are translocated into the nucleus. Once in the nucleus dPER and dTIM function as negative regulators of their own transcription, accumulation of dPER and dTIM declines, and activation of dper and dtim by dCLOCK/dBMAL starts again (Zylka, M. J. et al. (1998) Neuron 20, 1103-1110; Lowrey, P. L. et al. (2000) 288, 483-491). The dper gene has been shown to be a necessary element in controlling circadian rhythms in adult eclosion (the emergence of the adult fly from the pupa) behavior and locomotor activity (Konopka, R. J., & Benzer, S. (1971) Proc. Natl. Acad. Sci. USA, 68, 2112-2116). Missense mutations of the per gene can either shorten ($per^S$) or lengthen ($per^L$) the period of circadian rhythms, while nonsense mutations ($per^0$) cause arrhythmicity in their behaviors (Hall, J. C. (1995) Trends Neurosci. 18, 230-240).

In mammals, the suprachiasmatic nuclei (SCN) of the anterior hypothalamus are the site of a master biological clock (for review see Panda et al, (2002) Nature 417, 329-335; Reppert, S. M. and Weaver, D. R. (1997) Cell, 89, 487-490). The SCN clock is entrained to the 24 hour day by the daily light-dark cycle, with light acting through both direct and indirect retina-to-SCN pathways (Klein, D. C. et al. (1991) Suprachiasmatic Nuclei: The Mind's Clock, Oxford University Press, New York). In the SCN of rodents, three Per genes have been identified and cloned, and are designated as mouse Per1 (mPer1), mPer2 and mPer3. The protein products of these mammalian genes (mPER1, mPER2, mPER3) share several regions of homology to each other, and each mammalian Per gene encodes a protein with a protein dimerization domain designated as PAS (PAS is an acronym for the first three proteins PER, ARNT and SIM found to share this functionally important dimerization domain) that is highly homologous to the PAS domain of insect PER. All Per messenger RNAs (mRNAs) and protein levels oscillate during the circadian day and are intimately involved in both positive and negative regulation of the biological clock, but only mPER1 and mPER2 oscillate in response to light (Zylka, M. J. et al. (1998) Neuron 20, 1103-1110; Albrecht, U. et al., (1997) Cell 91, 1055-1064; Shearman, L. P. et al. (1997) Neuron 19, 1261-1269). The mammalian homolog of the *Drosophila* tim gene was cloned and designated as mTim. However, there was no evidence for mPER-mTIM interactions analogous to those observed in *Drosophila*, and it was suggested that PER-PER interactions may have replaced the function of PER-TIM dimers in the molecular workings of the mammalian circadian clock (Zylka, M. J. et al., (1998) Neuron 21, 1115-1122). Another possibility is that rhythms in PER1 and PER2 form negative feedback loops that regulate the transcriptional activity of the Clock protein (via their PAS domains), which, in turn, drives expression of either or both Per genes (Shearman, L. P. et al. (1997) Neuron 19, 1261-1269).

Understanding the roles of the three mPer genes in the mammalian clockwork has been the subject of much investigation. The structural homology of the mPER proteins to dPER led to the expectation that the mPER proteins would function as negative elements in the mammalian feedback loop. PER1 is believed to be involved in the negative regulation of its own transcription in the feedback loop, but recent evidence points to it being involved in the input pathway (Hastings, M. H. et al. (1999) Proc. Natl. Acad. Sci. USA 26, 15211-15216). PER2 is the most well characterized protein, and mPER2 mutant mice (mPer2$^{Brdm1}$), lacking 87 residues at the carboxyl portion of the PAS dimerization domain, have a shortened circadian cycle in normal light-dark settings, but show arrhythmicity in complete darkness. The mutation also diminishes the oscillating expression of both mPer1 and mPer2 in the SCN, indicating that mPer2 may regulate mPer1 in vivo (Zheng, B. et al. (1999) Nature 400, 169-173). PER2 has been shown to have a dual function in the regulation of the "gears" of the central clock (Shearman, L. P. et al. (2000) Science 288, 1013-1018). In that study, PER2 was shown to bind to cryptochrome (CRY) proteins and translocate to the nucleus where CRY negatively regulated transcription driven by the CLOCK and BMAL1 positive transcriptional complexes. Upon nuclear entry, PER2 initiated the positive arm of the clock by positively regulating BMAL1 transcription by a yet unidentified mechanism. The function of PER3 is poorly understood; however, in mPer3 knockout mice a subtle effect on circadian activity is observed, and therefore PER3 has been suggested to be involved in the circadian controlled output pathways (Shearman, L. P. et al. (2000) Mol. Cell. Biol. 17, 6269-6275). It has been reported that mPER proteins interact with each other and that mPER3 can serve as a carrier of mPER1 and mPER2 to bring them into the nucleus which is critical for the generation of circadian signals in the SCN (Kume, K. et al. (1999) Cell 98, 193-205; Takano, A. et al. (2000), FEBS Letters, 477, 106-112).

Phosphorylation of the components of the circadian clock has been postulated to regulate the duration of the cycle. The first genetic evidence that a specific protein kinase regulates the *Drosophila* circadian rhythm was the discovery of the novel gene doubletime (dbt), encoding a protein serine/threonine kinase (DBT) (Price J. L. et al. (1998) Cell 94, 83-95; Kloss B. et al. (1998) Cell 94, 97-107). Missense mutations in the dbt result in an altered circadian rhythm. Null alleles of dbt result in hypophosphorylation of dPER and arrhythmia.

The mammalian kinases most closely related to DBT are casein kinase Iε (CKIε) and casein kinase Iδ (CKIδ). Both kinases have been shown to bind to mPER1, and several studies have shown that CKIε phosphorylates both mouse and human PER1 (Price J. L. et al. (1998) Cell 94, 83-95; Kloss B. et al. (1998) Cell 94, 97-107). In a study with human embryonic kidney 293T cells co-transfected with wild-type hCKIε, hPER1 showed a significant increase in phosphorylation (evidenced by a shift in molecular mass). In this study, the phosphorylated hPER1 had a half-life of approximately twelve hours whereas unphosphorylated hPER1 remained stable in the cell for more that 24 hours, suggesting phosphorylation of hPER1 leads to a decrease in protein stability (Kessler, G. A. et al. (2000) NeuroReport, 11, 951-955). Another study also showed the consequence of PER1 phosphorylation by hCKIε includes both cytoplasmic retention and protein instability (Vielhaber, E. et al. (2000) Mol. Cell. Biol. 13, 4888-4899; Takano, A. et al. (2000) FEBS Letters 477, 106-112).

There has been no biochemical reason to choose between CKIε or CKIδ as a potential regulator in mammals until Lowery et al. [(2000) Science 288, 483-491] found that in the Syrian Golden hamster, semidominant mutations in CKIε (tau mutation, Ralph, M. R. and Menaker, M. (1988) Science 241, 1225-1227) caused a shortened circadian day in both heterozygous (22 h) and homozygous animals (20 h). In this instance, reduced levels of CKIε activity resulted in less PER phosphorylation with presumably higher levels of cytoplasmic PER protein leading to enhanced nuclear entry and altered circadian cycles. More recently, it has been suggested that CKIδ may also be involved in regulating circadian rhythmicity by post-translation modification of mammalian clock proteins hPER1 and hPER2 [Camacho, F. et al., (2001) FEBS Letters 489(2,3), 159-165]. Thus, inhibitors, including small molecule inhibitors, of mammalian or human CKIε and/or CKIδ provide a novel means to phase shift or reset the circadian clock. As discussed below, the alteration of circadian rhythm may find utility for the treatment of sleep or mood disorders.

U.S. Pat. No. 6,555,328 B1 discloses screening methods in cells to identify compounds that alter circadian rhythms based on a test compound altering the ability of human casein kinase 1ε and/or human casein kinase 1δ to phosphorylate the human clock proteins hPER1, hPER2 and hPER3. For example, HEK293T cells are co-transfected with hCKIε and Per1 or Per2. For the purpose of evaluating the relevancy of CKIε inhibition and CKIε inhibitors to circadian biology, a high-throughput cellular assay (33$^{rd}$ Annual Meeting, Soc. for Neurosci., Nov. 8-12, 2003, Abstract numbers 284.1, 284.2, and 284.3) was developed in which circadian rhythm could be monitored in a routine manner. The assay consists of Rat-1 fibroblasts stably expressing an Mper1-luc construct, thus enabling the determination of the rhythmic activation of the Mper1 promoter in living cells by repeatedly estimating luciferase activity by monitoring light-output over several days. The repeated measure format of the assay permits accurate and reproducible assessment of the concentration-dependent effects of CKIε inhibitors on circadian rhythm and provides the nexus for relating CKIε inhibition to circadian period alteration.

Sleep disorders have been classified into four major categories that include primary sleep disorders (dyssomnias and parasomnias), sleep disorders associated with medical/psychiatric disorders and a category of proposed sleep disorders for sleep disorders that cannot be classified due to insufficient data. Primary sleep disorders are thought to arise from abnormalities in the intrinsic systems responsible for sleep-wake generation (homeostatic system) or timing (circadian system). Dyssomnias are disorders in initiating or maintaining sleep and include primary insomnia, hypersomnia (excessive sleepiness), narcolepsy, breathing-related sleep disorder, circadian rhythm sleep disorder, and dyssomnias not otherwise specified. Primary insomnia is characterized by the persistence (>1 month) in difficulty of initiating and maintaining sleep or of non-restorative sleep. Difficulties in sleeping associated with primary insomnia leads to significant distress or impairment, including daytime irritability, loss of attention and concentration, fatigue and malaise, and deterioration of mood and motivation. Circadian rhythm sleep disorders include jet lag syndrome, shift work sleep disorder, advanced sleep phase syndrome and delayed sleep phase syndrome (J. Wagner, M. L. Wagner and W. A. Hening, Annals of Pharmacotherapy (1998) 32, 680-691). Individuals in a forced sleep paradigm demonstrate a greater wakefulness, as a percentage of sleep time, at certain periods of circadian day (Dijk and Lockley, J. Appl. Physiol. (2002) 92, 852-862). It has been generally accepted that with age there is an advance in our circadian rhythm for sleep and often results in less quality sleep (Am J Physiol Endocrinol Metab. (2002) 282, E297-E303). Thus, sleep occurring out of circadian phase may suffer in qualitative and quantitative terms, as further exemplified by alterations in sleep with shift work and jet lag. Disturbance of the human circadian clock can cause sleep disorders and agents that modulate circadian rhythmicity, such as an inhibitor of CKIε and/or CKIδ, may be useful for the treatment of sleep disorders, and particularly circadian rhythm sleep disorders.

Mood disorders are divided into depressive disorders ("unipolar depression"), bipolar disorders, and two disorders based on etiology that include mood disorder due to a general medical condition and substance-induced mood disorder. Depressive disorders are subclassified as major depressive disorder, dysthymic disorder and depressive disorder not otherwise specified. Bipolar disorders are subclassified as bipolar I disorder and bipolar II disorder. It has been observed that the specifier "seasonal pattern" can be applied to major depressive disorders that are recurrent and to the pattern of major depressive episodes in bipolar I disorder and bipolar II disorder. Prominent anergy, hypersomnia, overeating, weight gain, and a craving for carbohydrates often characterize major depressive episodes that occur in a seasonal pattern. It is unclear whether a seasonal pattern is more likely in major depressive disorder that is recurrent or in bipolar disorders. However, within the bipolar disorders, a seasonal pattern appears to be more likely in bipolar II disorder than in bipolar I disorder. In some individuals the onset of manic or hypomanic episodes may also be linked to a particular season. The winter-type seasonal pattern appears to vary with latitude, age and sex. Prevalence increases with higher latitudes, younger persons are at higher risk for winter depressive episodes, and females comprise 60% to 90% of persons with seasonal pattern. Seasonal affective disorder (SAD), a term commonly used in the literature, is a subtype of mood disorder that in the Diagnostic and Statistical Manual of Mental Disorders IV (DSM-IV) (American Psychiatric Association: "Diagnostic and Statistical Manual of Mental Disorders", Fourth Edition, Text Revision. Washington, D.C., American Psychiatric Association, 2000) is denoted by the term "with seasonal pattern" when describing a seasonal pattern of major depressive episodes in bipolar I disorder, bipolar II disorder or recurrent major depressive disorder (E. M. Tam et al., Can. J. Psychiatry (1995) 40, 457-466). The characteristics and diagnoses of depressive disorders, major depressive disorder, major depressive episode, bipolar I disorder, bipolar II disorder and seasonal effects are described in DSM-IV, Patients suffering from major depressive disorders, including SAD that is characterized by recurrent depressive episodes typically in winter, have been shown to be positively responsive to light therapy (Kripke, Journal of Affective Disorders (1998) 49(2), 109-117). The success of bright light treatment for patients with SAD and major depression resulted in the proposal of several hypotheses to explain the underlying mechanism of action for the therapeutic effect of light. These hypotheses included the "circadian rhythm hypothesis" that suggests the antidepressant effect of bright light could be associated with phase-shifting the circadian pacemaker relative to sleep (E. M. Tam et al., Can. J. Psychiatry (1995) 40, 457-466). In support of the link between light therapy and circadian rhythm, clinically effective light therapy in major depressive disorders causes a concomitant shift in circadian phase and the clinical effectiveness of light therapy appears to depend on the phase-shifting ability of the light therapy (Czeisler et al., The Journal of Physiology (2000) 526 (Part 3), 683-694; Terman et al., Arch. Gen. Psychiatry (2001) 58, 69-75). Additionally, light-therapy has been shown to accelerate and augment the effectiveness of the pharmacological treatment of major depressive disorders (Benedetti et al., J. Clin. Psychiatry (2003) 64, 648-653). Thus, inhibition of casein kinase Iε and/or casein kinase Iδ would be expected to cause a circadian phase shift and such inhibition represents a potential clinically effective mono- or combined therapy for mood disorders.

It should be noted that sleep disturbance is a criterion symptom for many psychiatric disorders (W. V. McCall, J. Clin. Psychiatry (2001) 62 (suppl 10), 27-32). Sleep disturbances are a common feature of depressive disorders and insomnia is the sleep disturbance that is frequently reported in depression, occurring in over 90% of depressed patients (M. E. Thase, J. Clin. Psychiatry (1999) 60 (suppl 17), 28-31). Accumulating evidence supports a common pathogenesis for primary insomnia and major depressive disorder. It has been hypothesized that corticotrophin releasing factor (CRF) hyperactivity (due to genetic predisposition or possibly early stress) and stress induce a process leading to exaggerated and protracted sleep disturbances, and eventually primary insomnia. Circadian rhythmicity in CRF secretion under non-stressed conditions may play a role in the normal sleep-wake expression (G. S. Richardson and T. Roth, J. Clin Psychiatry (2001) 62 (suppl 10), 39-45). Thus, agents that modulate circadian rhythmicity, for example by inhibition of casein kinase Iε and/or casein kinase Iδ, may be useful for treatment of depressive disorders due to effects on CRF secretion.

All of the references referred to hereinabove are incorporated herein by reference in their entirety.

Thus it is an object of this invention to provide methods of using 3-arylthioindole-2-carboxamides, 5-substituted-3-arylthioindole-2-carboxamides and related analogues as inhibitors of human casein kinase Iε phosphorylation of the human clock protein Period (hPER) which are therefore useful, as pharmaceutical agents, especially in the treatment and/or prevention of diseases and disorders associated with the central nervous system. This object and other objects of this invention become apparent from the detailed discussion of the invention that follows.

SUMMARY OF THE INVENTION

Thus, in accordance with the practice of this invention, there is provided methods for inhibiting human casein kinase Iε activity and phosphorylation of the human clock protein period (hPER) for the treatment of diseases or disorders of the central nervous system associated with the disturbance of the human circadian clock such as, for example, mood disorders including major depressive disorder, bipolar I disorder and bipolar II disorder, and sleep disorders including circadian rhythm sleep disorders such as, for example, shift work sleep disorder, jet lag syndrome, advanced sleep phase syndrome and delayed sleep phase syndrome that comprises administering to a patient in need of such treatment a therapeutically effective amount of a compound of formula I.

Accordingly, a broad embodiment of the invention is directed to a method for treating a patient suffering from a disease or disorder ameliorated by inhibition of casein kinase Iε activity comprising administering to said patient a therapeutically effective amount of a compound of formula I:

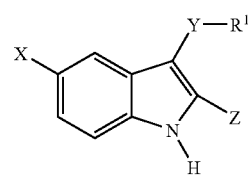

wherein
X is H, Cl, F, Br, $NO_2$, CN, $OR^2$, $NR^2R^2$, $HNSO_2$—$C_{1-3}$alkyl, or NHCO—$C_{1-3}$alkyl;
Y is —S(O)$_n$— or —O— wherein n is 0, 1 or 2;
$R^1$ is
1) aryl, unsubstituted or substituted with one or more of:
   a) $C_{1-5}$alkoxy,
   b) OH,
   c) halogen,
   d) $NR^2R^2$, or
   e) $C_{1-5}$alkyl, unsubstituted or substituted with one or more of:
      i) OH or
      ii) $C_{1-5}$alkoxy;
2) heterocycle, unsubstituted or substituted with one or more of:
   a) $C_{1-5}$alkyl, unsubstituted or substituted with one or more of:
      i) OH or
      ii) $C_{1-5}$alkoxy,
   b) $C_{1-5}$alkoxy,
   c) OH,
   d) halogen, or
   e) $NR^2R^2$;
3) $C_{1-5}$alkyl, unsubstituted or substituted with one or more of:
   a) $C_{1-5}$alkyl,
   b) $C_{1-5}$alkoxy,
   c) OH, or
   d) aryl, unsubstituted or substituted with one or more of:
      i) $C_{1-5}$alkyl,
      ii) $C_{1-5}$alkoxy,
      iii) OH,
      iv) halogen, or
      v) $NR^2R^2$
Z is
1) C(=O)$NR^2R^3$ or
2) C(=O)$R^4$;
$R^2$ is hydrogen or $C_{1-3}$alkyl;
$R^3$ is hydrogen, $C_{1-5}$alkyl, or $C_{3-6}$cycloalkyl;
$R^4$ is 1-piperidinyl, 1-pyrrolidinyl, 1-piperazinyl or 4-morpholinyl, unsubstituted or substituted with one or more of:
1) $C_{1-5}$alkyl,
2) $C_{1-5}$alkoxy,
3) OH,
4) halogen, or
5) $NR^2R^2$;
or a stereoisomer, an enantiomer, a racemate or a tautomer of said compound, or a pharmaceutically acceptable salt thereof.

Another embodiment of the present invention relates to a method for inhibiting casein kinase Iε activity in a patient comprising administering to said patient a therapeutically effective amount of a compound of formula I, or a stereoisomer, an enantiomer, a racemate or a tautomer of said compound, or a pharmaceutically acceptable salt thereof,

DETAILED DESCRIPTION OF THE INVENTION

As used herein, "stereoisomer" is a general term used for all isomers of individual molecules that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers). The compounds of the present invention may have asymmetric centers and occur as racemates, racemic mixtures, individual diastereoisomers, or enantiomers, or may exist as geometric isomers, with all isomeric forms of said compounds being included in the present invention.

As used herein, "R" and "S" are used as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counter-clockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon at the chiral center and "L", that of the isomer in which it is on the left.

As used herein, "tautomer" or "tautomerism" refers to the coexistence of two (or more) compounds that differ from each other only in the position of one (or more) mobile atoms and in electron distribution, for example, keto-enol tautomers or tautomerism.

As used herein, "alkyl" refers to a saturated linear or branched chain aliphatic hydrocarbon group having from one to five carbon atoms, and includes methyl, ethyl, propyl, isopropyl, butyl, sec-butyl, tert-butyl and the like groups.

As used herein, "alkoxy" refers to a monovalent substituent which consists of a linear or branched alkyl chain having from one to five carbon atoms linked through an ether oxygen atom and having its free valence bond from the ether oxygen, and includes methoxy, ethoxy, propoxy, isopropoxy, butoxy, sec-butoxy, tert-butoxy and the like groups.

As used herein the term "$C_{3-6}$cycloalkyl" refers to a saturated monocyclic hydrocarbon ring structure containing from three to six carbon atoms and includes cyclopropyl, cyclobutyl, cyclopentyl, cyclohexyl, and the like.

As used herein, "aryl" or "Ar" means any stable monocyclic, bicyclic or tricyclic carbon ring of up to seven members in each ring, wherein at least one ring is aromatic and unsubstituted or substituted with from one to three substituents selected from the group consisting of hydroxy, $C_{1-5}$alkoxy, halogen, —$NH_2$, —NH($C_{1-3}$alkyl), —N($C_{1-3}$alkyl)$_2$, and $C_{1-5}$alkyl unsubstituted or substituted with one or more of OH or $C_{1-5}$alkoxy. Examples of "aryl" or "Ar" include phenyl, naphthyl, tetrahydronaphthyl and biphenyl. The term "aryl-($C_{1-5}$alkyl)" includes 4-methylphenyl, 2-methylphenyl, phenylmethyl(benzyl), phenylethyl, p-methoxybenzyl, p-fluorobenzyl and p-chlorobenzyl.

As used herein, the term "acyl" refers to a linear or branched saturated aliphatic hydrocarbon group having the from one to six carbon atoms attached to a carbonyl (C=O) moiety and having its free valence bond from the carbonyl moiety. The term "acyl" includes acetyl, propionyl, butyryl, isobutyryl, and the like.

As used herein, "heterocycle" or "heterocyclic" means a stable 5- to 7-membered monocyclic or stable 8- to 11-membered bicyclic heterocyclic ring which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolidinyl, 2-oxoazepinyl, azepinyl, pyrrolyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoxazolyl, furyl, tetrahydrofuryl, benzofuranyl, tetrahydropyranyl, thienyl, benzothienyl, thiomorpholinyl, thiomorpholinyl sulfoxide, thiomorpholinyl sulfone, and oxadiazolyl.

As used herein, "halogen", "hal" or "halo" refers to a member of the family of fluorine, chlorine, bromine or iodine.

When any variable (e.g., aryl, heterocycle, $R^1$, $R^2$, $R^3$, $R^4$, X, Y, Z, etc.) occurs more than one time in any constituent or in formula I of this invention, its definition on each occurrence is independent of its definition at every other occurrence. Also, combinations of substituents and/or variables are permissible only if such combinations result in stable compounds.

As used herein, "treat", "treating" or "treatment" refers to:
(i) preventing a disease, disorder or condition from occurring in a patient that may be predisposed to the disease, disorder and/or condition, but has not yet been diagnosed as having it;
(ii) inhibiting a disease, disorder or condition, i.e., arresting its development; or
(iii) relieving a disease, disorder or condition, i.e., causing regression of the disease, disorder and/or condition.

As used herein, the term "patient" refers to a warm blooded animal such as a mammal which is afflicted with a particular disease, disorder or condition. It is explicitly understood that guinea pigs, dogs, cats, rats, mice, horses, cattle, sheep, and humans are examples of animals within the scope of the meaning of the term.

As used herein, "disease" refers to an illness, sickness or an interruption, cessation or disorder of body functions, systems or organs.

As used herein, "disorder" refers to a disturbance of function, structure or both resulting from a genetic or embryologic failure in development, or from exogenous factors such as poison, injury or disease.

As used herein, "condition" refers to a state of being, health or physical fitness.

As used herein, "prophylaxis" refers to the prevention of disease.

As used herein, the term "sleep disorder", "sleep disorders" or "sleep disturbance" means insomnia.

As used herein, the term "insomnia" means the inability to sleep in the absence of external impediments, such as noise, bright light, etc., during the period when sleep should normally occur and the inability to sleep may vary in degree from restlessness or disturbed slumber to a curtailment of the normal length of sleep or to absolute wakefulness. The term "insomnia" includes primary insomnia, insomnia related to a mental disorder, substance-induced insomnia and circadian rhythm insomnia that is insomnia due to a change in the normal sleep-wake schedule (shift changes, shift work sleep disorder, jet lag or jet lag syndrome, etc.).

As used herein the term "primary insomnia" means difficulty in initiating sleep, in maintaining sleep or having restorative sleep which is not caused by a mental disorder or due to physiological effects of taking or withdrawing from certain substances (substance-induced insomnia).

As used herein the term "circadian rhythm sleep disorder" includes jet lag or jet lag syndrome, shift work sleep disorder, advanced sleep phase syndrome and delayed sleep phase syndrome.

As used herein the term "effective inhibitory amount of a compound" or "effective casein kinase Iε inhibitory amount of a compound" means enough of a compound that becomes bioavailable through the appropriate route of administration to treat a patient afflicted with a disease, disorder or condition amenable to such treatment.

As used herein the term "a therapeutically effective amount" means an amount of a compound which is effective in treating the named disease, disorder or condition.

As used herein, the phrase "lengthening of circadian rhythm period" refers to increasing the interval between seminal events in a process that occurs regularly with a frequency of approximately once every 24 hours.

As used herein, the phrase "shortening of circadian rhythm period" refers to decreasing the interval between seminal events in a process that occurs regularly with a frequency of approximately once every 24 hours.

As used herein, the term "pharmaceutically acceptable salt" is intended to apply to any salt, whether previously known or future discovered, that is used by one skilled in the art that is a non-toxic organic or inorganic addition salt which is suitable for use as a pharmaceutical. Illustrative bases which form suitable salts include alkali metal or alkaline-earth metal hydroxides such as sodium, potassium, calcium or magnesium hydroxides; ammonia and aliphatic, cyclic or aromatic amines such as methylamine, dimethylamine, triethylamine, diethylamine, isopropyldiethylamine, pyridine and picoline. Illustrative acids which form suitable salts include inorganic acids such as, for example, hydrochloric, hydrobromic, sulfuric, phosphoric and like acids, and organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids, and organic sulfonic acids such as methanesulfonic, p-toluenesulfonic, 1-naphthalenesulfonic, 2-naphthalenesulfonic and like acids.

As used herein, "pharmaceutical carrier" or "pharmaceutically acceptable carrier" refers to known pharmaceutical excipients useful in formulating therapeutically active compounds for administration, and which are substantially non-toxic and non-sensitizing under conditions of use. The exact proportion of these excipients is determined by the solubility and chemical properties of the active compound, the chosen route of administration as well as standard pharmaceutical practice. In practicing the methods of this invention, the active ingredient is preferably incorporated into a composition containing a pharmaceutical carrier, although the compounds are effective and can be administered, in and of themselves. That said, the proportion of active ingredient can vary from about 5 to 90% by weight.

Further abbreviations that may appear in this application are as follows:
Me (methyl), Et (ethyl), Ph (phenyl), $Et_3N$ (triethylamine), p-TsOH (para-toluene sulfonic acid), TsCl (para-toluenesulfonyl chloride), hept (heptane), DMF (dimethylformamide), NMP (1-methyl-2-pyrrolidinone or N-methyl-2- pyrrolidinone), IPA (isopropanol or isopropyl alcohol), TFA (trifluoroacetic acid), DBU (1,8-diazabicyclo[5.4.0]undec-7-ene), DBN (1,5-diazabicyclo[4.3.0]non-5-ene), rt or r.t. (room temperature or ambient temperature), min or min. (minutes), h (hour or hours), UV (ultraviolet), LCMS (liquid chromatography mass spectrometry), t-Boc or Boc (tert-butoxycarbonyl), Bn (benzyl), t-Bu (tertiary butyl). i-Pr (isopropyl), TFA (trifluoroacetic acid), HOAc (acetic acid), EtOAc (ethyl acetate), Et$_2$O (diethylether), EtOH (ethanol), g (gram), mg (milligram), μg (microgram), ng (nanogram), mL (milliliter), μL (microliter), L (liter), HPLC (high-performance liquid chromatography), TLC, tlc or Tlc (thin layer chromatography), g/L (grams per liter), SiO$_2$ (silica gel), L/min (liters per minute), mL/min (milliliters per minute), mmol (millimole), M (molar), mM (millimolar), μM (micromolar), nM (nanomolar), μCi (microCurie), CPM (counts per minute), rpm (revolutions per minute), mm (millimeter), μm (micrometer), μ (micron), nm (nanometer), ppm (parts per million), psi (pounds per square inch), eq. or equiv. (equivalent), R$_T$ (retention time), ° C. (degrees Celsius), and K (Kelvin).

Accordingly, a broad embodiment of the invention is directed to a method for treating a patient suffering from a disease or disorder ameliorated by inhibition of casein kinase Iε activity comprising administering to said patient a therapeutically effective amount of a compound of formula I, or a stereoisomer, an enantiomer, a racemate or a tautomer of said compound, or a pharmaceutically acceptable salt thereof,

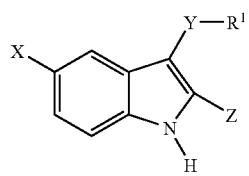

I wherein:
X is H, Cl, F, Br, NO$_2$, CN, OR$^2$, NR$^2$R$^2$, HNSO$_2$—C$_{1-3}$alkyl, or NHCO—C$_{1-3}$alkyl;
Y is —S(O)$_n$— or —O— wherein n is 0, 1 or 2;
R$^1$ is
  1) aryl, unsubstituted or substituted with one or more of C$_{1-5}$alkoxy, OH, halogen, NR$^2$R$^2$ or C$_{1-5}$alkyl unsubstituted or substituted with one or more of OH or C$_{1-5}$alkoxy,
  2) heterocycle, unsubstituted or substituted with one or more of C$_{1-5}$alkyl unsubstituted or substituted with one or more of OH or C$_{1-5}$alkoxy, C$_{1-5}$alkoxy, OH, halogen, or NR$^2$R$^2$;
  3) C$_{1-5}$alkyl, unsubstituted or substituted with one or more of C$_{1-5}$alkyl, C$_{1-5}$alkoxy, OH, or aryl unsubstituted or substituted with one or more of C$_{1-5}$alkyl, C$_{1-5}$alkoxy, OH, halogen, or NR$^2$R$^2$;
Z is C(=O)NR$^2$R$^3$ or C(=O)R$^4$;
R$^2$ is hydrogen or C$_{1-3}$alkyl;
R$^3$ is hydrogen, C$_{1-5}$alkyl, or C$_{3-6}$cycloalkyl;
R$^4$ is 1-piperidinyl, 1-pyrrolidinyl, 1-piperazinyl or 4-morpholinyl, unsubstituted or substituted with one or more of C$_{1-5}$alkyl, C$_{1-5}$alkoxy, OH, halogen, or NR$^2$R$^2$.

A second embodiment of the invention is directed to a method for treating a patient suffering from a disease or disorder ameliorated by inhibition of casein kinase Iε activity wherein said inhibition of casein kinase Iε activity results in a lengthening circadian rhythm period.

A third embodiment of the invention is directed to a method for treating a patient suffering from a disease or disorder ameliorated by inhibition of casein kinase Iε wherein the disease or disorder is a mood disorder or a sleep disorder.

A fourth embodiment of the invention is directed to a method for treating a patient suffering from a disease or disorder ameliorated by inhibition of casein kinase Iε wherein the disorder is a mood disorder.

A fifth embodiment of the invention is directed to a method for treating a patient suffering from a disease or disorder ameliorated by inhibition of casein kinase Iε wherein the disease or disorder is a mood disorder selected from the group consisting of a depressive disorder and a bipolar disorder.

A sixth embodiment of the invention is directed to a method for treating a patient suffering from a depressive disorder wherein the depressive disorder is major depressive disorder.

A seventh embodiment of the invention is directed to a method for treating a patient suffering from a disease or disorder ameliorated by inhibition of casein kinase Iε wherein the disorder selected from the group consisting of bipolar I disorder and bipolar II disorder.

An eighth embodiment of the invention is directed to a method for treating a patient suffering from a disease or disorder ameliorated by inhibition of casein kinase Iε wherein the disorder is a sleep disorder.

A ninth embodiment of the invention is directed to a method for treating a patient suffering from a sleep disorder wherein the sleep disorder is a circadian rhythm sleep disorder.

A tenth embodiment of the invention is directed to a method for treating a patient suffering from a disease or disorder ameliorated by inhibition of casein kinase Iε wherein the disease or disorder is a circadian rhythm sleep disorder selected from the group consisting of shift work sleep disorder, jet lag syndrome, advanced sleep phase syndrome and delayed sleep phase syndrome.

A eleventh embodiment of this invention encompasses a method for treating a patient suffering from a disease or disorder ameliorated by inhibition of casein kinase Iε activity comprising administering to said patient a therapeutically effective amount of a compound of formula I wherein Y is S(O)$_2$, Z is C(=O)NH$_2$ or C(=O)NHCH$_3$, and R$^1$ is phenyl or pyridinyl.

One class of compounds within the eleventh embodiment is further limited to compounds of formula I wherein Y is S(O)$_2$, Z is C(=O)NH$_2$, and R$^1$ is phenyl. The following compounds are representative examples within the scope of this embodiment:
3-benzensulfonyl-5-chloro-1H-indole-2-carboxylic acid amide, and
3-benzensulfonyl-1H-indole-2-carboxylic acid amide.

A second class of compounds within the eleventh embodiment is further limited to compounds of formula I wherein Y is S, Z is C(=O)NHCH$_3$, and R$^1$ is phenyl or pyridinyl. The following compounds are representative examples within the scope of this embodiment:
3-phenylsulfanyl-1H-indole-2-carboxylic acid methylamide, and
3-(pyridin-2-ylsulfanyl)-1H-indole-2-carboxylic acid methylamide A twelfth embodiment of this invention encompasses a method for treating a patient suffering from a disease or disorder ameliorated by inhibition of casein kinase Iε activity comprising administering to said patient a therapeutically effective amount of a compound of formula I wherein Y is O, Z is C(=O)NH$_2$, and R$^1$ is phenyl, substituted phenyl, C$_{1-5}$alkyl or substituted C$_{1-5}$alkyl. The following compounds are representative examples within the scope of this embodiment:
3-phenoxy-1H-indole-2-carboxylic acid amide,
3-(4-methoxy-phenoxy-1H-indole-2-carboxylic acid amide,
3-(4-fluoro-phenoxy-1H-indole-2-carboxylic acid amide,
3-(2-fluoro-phenoxy-1H-indole-2-carboxylic acid amide,
3-(4-chloro-phenoxy-1H-indole-2-carboxylic acid amide,
3-methoxy-1H-indole-2-carboxylic acid amide, 3-ethoxy-1H-indole-2-carboxylic acid amide,
3-isopropoxy-1H-indole-2-carboxylic acid amide,
3-tert-butoxy-1H-indole-2-carboxylic acid amide, and
3-benzyloxy-1H-indole-2-carboxylic acid amide.

A thirteenth embodiment of this invention encompasses a method for treating a patient suffering from a disease or disorder ameliorated by inhibition of casein kinase Iε activity comprising administering to said patient a therapeutically effective amount of a compound of formula I wherein Y is S, S(O), or S(O)$_2$, Z is C(=O)R$^4$, and R$^4$ is 1-piperidinyl, 1-pyrrolidinyl, 1-piperazinyl or 4-morpholinyl. The following compounds are representative examples within the scope of this embodiment:
(3-benzenesulfonyl-5-chloro-1H-indol-2yl)-morpholin-4-yl-methanone,
(5-fluoro-3-p-tolylsulfanyl-1H-indol-2-yl)-pyrrolidin-1-yl-methanone,
(3-phenylsulfanyl-1H-indol-2yl)-piperidin-1-yl-methanone,
(5-fluoro-3-phenylsulfanyl-1H-indol-2-yl)-pyrrolidin-1-yl-methanone,
[3-(2-amino-phenylsulfanyl)-1H-indol-2-yl]-pyrrolidin-1-yl-methanone,
[3-(2-amino-phenylsulfanyl)-1H-indol-2-yl]-piperidin-1-yl-methanone,
[3-(2-amino-phenylsulfanyl)-5-fluoro-1H-indol-2-yl]-piperidin-1-yl-methanone,
[5-fluoro-3-(p-toluene-4-sulfinyl)-1H-indol-2-yl]-pyrrolidin-1-yl-methanone,
(3-phenylsulfanyl-1H-indol-2-yl)-piperazin-1-yl-methanone hydrochloride,
[5-fluoro-3-(pyridin-2-ylsulfanyl)-1H-indol-2-yl]-pyrrolidin-1-yl-methanone,
[3-(pyridin-2-ylsulfanyl)-1H-indol-2-yl]-pyrrolidin-1-yl-methanone,
piperidin-1-yl-[3-(pyridin-2-ylsulfanyl)-1H-indol-2-yl]-methanone, and
[5-fluoro-3-(pyridin-2-ylsulfanyl)-1H-indol-2-yl]-piperidin-1-yl-methanone.

A fourteenth embodiment of this invention encompasses a method for treating a patient suffering from a disease or disorder ameliorated by inhibition of casein kinase Iε activity comprising administering to said patient a therapeutically effective amount of a compound of formula I wherein Y is S, Z is C(=O)NH$_2$, and R$^1$ is pyridinyl. The following compound is a representative example within the scope of this embodiment:
3-(pyridin-2-ylsulfanyl)-1H-indole-2-carboxylic acid amide.

A fifteenth embodiment of this invention encompasses a method for treating a patient suffering from a disease or disorder ameliorated by inhibition of casein kinase Iε activity comprising administering to said patient a therapeutically effective amount of a compound of formula I wherein Y is S, Z is C(=O)NH$_2$, and R$^1$ is phenyl or substituted phenyl. The following compounds are representative examples within the scope of this embodiment:
3-phenylsulfanyl-1H-indole-2-carboxylic acid amide,
5-bromo-3-phenylsulfanyl-1H-indole-2-carboxylic acid amide,
3-(2-amino-phenylsulfanyl)-5-methoxy-1H-indole-2-carboxylic acid amide,
3-(3-fluoro-phenylsulfanyl-1H-indole-2-carboxylic acid amide,
3-(2-amino-phenylsulfanyl)-5-bromo-1H-indole-2-carboxylic acid amide, and
3-(2-amino-phenylsulfanyl)-1H-indole-2-carboxylic acid amide.

A sixteenth embodiment of this invention is directed toward a method for inhibiting casein kinase Iε activity in a patient comprising administering to said patient a therapeutically effective amount of a compound of formula I, or a stereoisomer, an enantiomer, a racemate or a tautomer thereof, resulting in a lengthening of circadian rhythm period.

All of the various embodiments of the present invention as disclosed herein can be used as methods of treating various diseases and disorders as described herein. As stated herein the compounds used in the method of this invention are capable of inhibiting the effects of casein kinase Iε. One skilled in the art readily appreciates that the diseases and disorders expressly stated herein are not intended to be limiting but rather to illustrate the efficacy of the compounds of the present invention. Thus, it is to be understood that the compounds of the invention may be used to treat any disease or disorder ameliorated by the inhibition of casein kinase Iε.

Chemical Syntheses

The compounds of the invention are prepared by methods well known to one skilled in the art. Specifically, the compounds of this invention are disclosed in U.S. Pat. No. 5,527,819, and can be prepared in accordance with the procedures provided therein, which is incorporated herein by reference in its entirety. Even more specifically, the various syntheses that can be employed for the preparation of the compounds of this invention are illustrated in Schemes 1, 2 and 3, and the methodology is described in detail by the examples that follow.

Formulations

The pharmaceutical compositions of the present invention are prepared in a manner well known in the pharmaceutical arts. The carrier or excipients may be a solid, semisolid or liquid material which can serve as a vehicle or medium for the active ingredient. Suitable carriers or excipients are well known in the art. The pharmaceutical composition may be adapted for oral, inhalation, parenteral or topical use, and may be administered to the patient in the form of tablets, capsules, suspensions, syrups, aerosols, inhalants, suppositories, salves, powders, solutions and the like. As used herein, the term "pharmaceutical carrier" or pharmaceutically acceptable carrier" means one or more excipients.

In preparing pharmaceutical compositions or formulations of the compounds of the present invention, care should be taken to ensure bioavailability of an effective therapeutic amount of the active compound or compounds by the selected route of administration, including oral, parenteral and subcutaneous routes. For example, effective routes of administration include subcutaneous, intravenous, transdermal, intranasal, rectal, vaginal and the like routes including release from implants as well as direct injection of the active ingredient and/or composition directly into the tissue.

For oral administration, the compounds of the present invention can be formulated into solid or liquid preparations, with or without inert diluents or edible carriers, such as capsules, pills, tablets, troches, powders, solutions, suspensions or emulsions. The capsules, pills, tablets, troches and the like may also contain one or more of the following adjuvants: binders such as microcrystalline cellulose, gum tragacanth; excipients such as starch or lactose, disintegrating agents such as alginic acid, corn starch and the like; lubricants such as stearic acid, magnesium stearate or Sterotex®, (Stokely-Van Camp Inc., Indianapolis, Ind.) glidants such as colloidal silicon dioxide; sweetening agents such as sucrose or saccharin; and flavoring agents such as peppermint, methyl salicylate or fruit flavoring. When the dosage unit form is a capsule, it may also contain a liquid carrier such as polyethylene glycol or a fatty oil. Materials used should be pharmaceutically pure and nontoxic in the amounts used.

For parenteral administration, the compounds of the present invention may be administered as injectable dosages of a solution or suspension of the compound in a physiologically acceptable diluent with a pharmaceutical carrier which can be a sterile liquid such as water-in-oil or without the addition of a surfactant and other pharmaceutically acceptable excipients. Illustrative oils which can be employed in the preparations are those of petroleum, animal, vegetable or synthetic origin such as, for example, peanut oil, soybean oil and mineral oil. In general, water, saline, aqueous dextrose and related sugar solutions, ethanol and glycols, such as propylene glycol are preferred liquid carriers, particularly for injectable solutions. The parenteral preparation can be enclosed in ampoules, disposable syringes or multiple dose vials made of inert plastic or glass.

The solutions or suspensions described above may also include one or more of the following adjuvants: sterile diluents such as water for injection, saline solution, fixed oils, polyethylene glycols, glycerin, propylene glycol or other synthetic solvents, antibacterial agents such as ascorbic acid or sodium bisulfite; chelating agents such as ethylenediaminetetra-acetic acid; buffers such as acetates, citrates or phosphates and agents for the adjustment of tonicity such as sodium chloride or dextrose.

The compounds of the present invention can be administered in the form of a cutaneous patch, a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones. Suitable pharmaceutical carriers and formulation techniques are found in standard texts, such as *Remington: The Science and Practice of Pharmacy*, 19th edition, Volumes 1 and 2, 1995, Mack Publishing Co., Easton, Pa., U.S.A., which is herein incorporated by reference.

In the treatment of various diseases, disorders and conditions as described herein, a suitable dosage level is about 0.01 mg/kg per day to about 250 mg/kg per day, preferably about 0.05 mg/kg per day to about 100 mg/kg per day, and especially about 0.05 mg/kg per day to about 40 mg/kg per day. The compounds of the present invention may be administered on a regimen of 1 to 4 times per day and as dictated by the nature of the disease, disorder or condition to be treated.

Schemes 1 to 3 for preparing the example compounds of the invention are presented below. Tables 1 and 2 illustrate the compounds that can be synthesized according to Schemes 1 to 3 and biological data for in vitro inhibition of casein kinase Iε by the example compounds is summarized in Table 3.

EXAMPLES

The following examples are intended to serve for illustration of the invention in greater detail, without restricting the breadth of the invention in any manner.

General Synthetic Methods

Unless otherwise noted, materials were obtained from commercial suppliers and used without further purification. All reactions were run under an inert atmosphere such as nitrogen or argon with anhydrous reagents and solvents. Flash chromatography was performed using EM Science silica gel 60 (40-63 mm) using the solvent systems as described. Thin layer chromatography was performed using 0.25 mm silica gel coated 60F-254 plates (EM) and visualized using iodine vapor, UV light, or a staining reagent such as $KMnO_4$ solution.

Infrared (IR) spectra were recorded on a Nexus 670 FTIR (Nicolet) spectrometer with samples prepared as indicated, and are reported in wave numbers ($cm^{-1}$). $^1H$ NMR spectra were recorded on a Varian Gemini and/or mercury 300, Unity 400, or Unity plus and/or Inova 500 MHz spectrometers with chemical shifts (δ) reported in ppm relative to tetramethylsilane (0.0 ppm) or chloroform (CDCl3, 7.26 ppm) as a reference. $^{13}C$ NMR spectra were recorded on the Varian Unity instrument (100.57 MHz, $^{13}C$ frequency) with chemical shifts (δ) reported in ppm relative to $CDCl_3$ (77.0 ppm), unless stated otherwise. Mass spectra (MS) were obtained on a Finnegan MAT Model TSQ 700 Mass Spectrometer System by chemical ionization at 120 eV using methane (CI, 120 eV). Liquid Chromatography Mass Spectrometry (LCMS) was performed on a Micromass LCT interfaced with a Gilson 215 liquid handler. High resolution mass spectrometric analysis (exact mass spectra) was performed in the ESI mode at mass resolution of 10,000 using a Micromass QTOF mass spectrometer. Exact mass values were determined for the protonated molecular ions (M+1) wherein M refers to the molecular ion.

Scheme 1
3-Arylthioindoles and Analogs

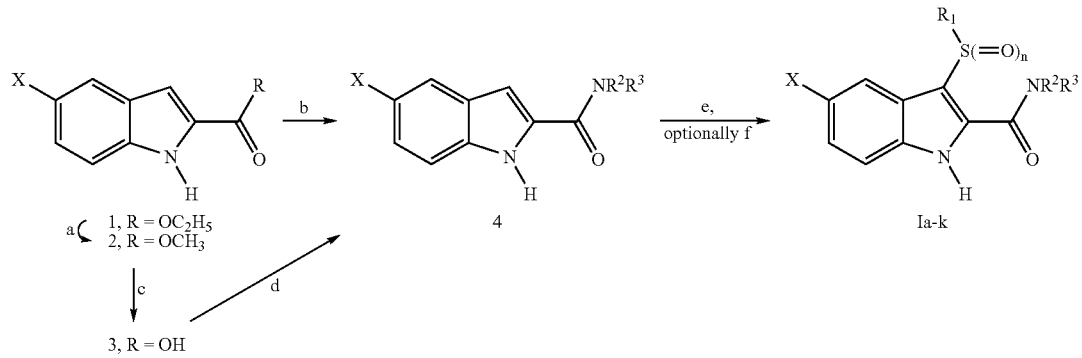

a) $K_2CO_3$, MeOH; b) $NH_4OH/LiCl$ or $NH_3/MeOH/LiCl$, or $Me_2NH/MeOH$ or $Me_2NH/H_2O$
c) $MeOH/H_2O/NaOH$ then HCl; d) carbonyldiimidazole and $NH_4OH$, or carbonyldiimidazole and a primary or secondary amine; e) NaH, DMF, $R^1$—S—S—$R^1$ or $Cs_2CO_3$, DMF, $R^1$—S—S—$R^1$ ($R^1$ = aryl); f) $H_2O_2$.

General Synthetic Procedure I (Trans-Esterification; Scheme I, Step a)

Add to ethyl indole-2-carboxylate 1 (42.3 mmol) in MeOH (50 mL), $K_2CO_3$ (1.20 equiv., 50.7 mmol) and stir the suspension with heating to 55° C. for 1 h. Monitor the reaction by tlc (ether/heptane) and when complete concentrate the reaction in vacuo, dilute with $H_2O$ and stir for 15 min. Collect the solid by filtration and dry under vacuum at 65° C. for 3 h to afford methyl indole-2-carboxylate 2.

General Synthetic Procedure II (Amidation using $NH_4OH$; Scheme I, Step b)

Stir a suspension of 1 or 2 (40.0 mmol) in $NH_4OH$ (100 mL) and LiCl (1.0 equiv.) at rt for 16 h. Filter the solid from the reaction mixture, wash with $H_2O$ and air dry to give the corresponding primary amide 4.

General Synthetic Procedure III (Amidation using $NH_3$/MeOH; Scheme I, Step b)

Stir ethyl indole-2-carboxylate 1 (X=H, 4.67 mmol) in 7N $NH_3$/MeOH (20 mL) and add LiCl (1.0 equiv., 4.67 mmol). Stir the reaction mixture at rt for 5 days monitoring by tlc (10% MeOH/$CH_2Cl_2$). Concentrate the mixture to minimum volume, dilute with $H_2O$ and collect the solid by filtration. Wash the filter cake with $H_2O$ and dry under vacuum at 60° C. to provide primary amide 4 (X=$R^2$=$R^3$=H), tlc $R_f$ (silica gel, 10% MeOH/$CH_2Cl_2$): 1 (X=H) 0.95, 2 (X=H) 0.93, 4 (X=$R^2$=$R^3$=H) 0.40.

General Synthetic Procedure IV (Hydrolysis of Methyl Ester 2 to Carboxylic Acid 3, Scheme I, Step c)

Add NaOH (82.0 mmol) to methyl indole-2-carboxylate 2 (27.0 mmol) as a suspension in MeOH/$H_2O$ (3:1, 160 mL). Stir at rt for 16 h, concentrate, and acidify with HCl. Collect the precipitate by filtration, wash with $H_2O$ and dry in vacuuo to afford indole-2-carboxylic acid 3.

General Synthetic Procedure V (Amidation of 2-indole Carboxylic Acid 3; Scheme I, Step d)

Add to a solution of indole-2-carboxylic acid 3 (31.0 mmol) and anhydrous THF (50 ml), carbonyldiimidazole (1.10 equiv., 5.5 g, 34.0 mmol). Stir for 1 h and add conc. $NH_4OH$ (50 mL) in one portion to the thick suspension. Stir at rt and after 16 h collect the solid by filtration, wash with $H_2O$ and dry in vacuuo at 40° C. to afford the indole-2-carboxamide 4 ($R^2$=$R^3$=H).

General Synthetic Procedure VIa (Amidation of 2-indole Carboxylic Acid 3 with Primary or Secondary Amines; Scheme I, Step d)

Add to a solution of indole-2-carboxylic acid 3 (12.4 mmol) and anhydrous THF (30 mL), carbonyldiimidazole (1.5 equiv., 18.6 mmol) and stir for 1 h. Then add the amine (for example, methylamine, pyrrolidine, piperidine, piperazine, benzylamine or morpholine, 3.0 equiv, 37.2 mmol)) in one portion and stir the reaction at rt. After 16 h, quench the reaction with water, collect the precipitate by filtration and dry under vacuum to afford the N-substituted-indole-2-carboxamide 4.

General Synthetic Procedure VIb (Amidation of Ethyl or Methyl Indole-2-carboxylate with Primary and Secondary Amines, Scheme I, Step b)

Stir ethyl indole-2-carboxylate 1 (X=H, 4.67 mmol) or methyl indole-2-carboxylate 2 (X=H, 4.67 mmol) in $Me_2NH/H_2O$ (50 mL, 40%). Stir the reaction mixture at rt for 16 h monitoring by tlc (10% MeOH/$CH_2Cl_2$). Concentrate the mixture to minimum volume, dilute with $H_2O$ and collect the solid by filtration. Wash the filter cake with $H_2O$ and dry under vacuum at 60° C. to provide dimethyl amide 4 (X=H, $R^2$=$R^3$=Me), tlc $R_f$=0.65 (silica gel, 10% MeOH/$CH_2Cl_2$).

General Synthetic Procedure VIIa (3-arylthioindoles using NaH; Scheme I, Step e)

Add to a stirred suspension of NaH (60% oil dispersion, 1.2 equiv., 9.8 mmol) in DMF (75 mL) under $N_2$ at rt, a solution of the indole-2-carboxyamide 4 (8.18 mmol) in DMF (5 mL). After 5 min. add the diaryldisulfide (1.0 equiv., 8.18 mmol) in one portion and heat the reaction with stirring to 95° C. for 16 h. Follow the reaction by partitioning an aliquot sample between EtoAc/$H_2O$ and analyzing the organic phase of the aliquot by thin layer chromatography on silica gel with 10% MeOH/$CH_2Cl_2$. Concentrate the reaction in vacuo, dilute with $H_2O$ and stir for 30 min. filter and air-dry. Chromatograph the crude solid on silica gel eluting with 9:1 $CH_2Cl_2$/MeOH to provide the 3-arylthio-substituted indole I.

General Synthetic Procedure VIIb (3-arylthioindoles using $Cs_2CO_3$, Scheme I, Step e)

Add to a solution of the indole-2-carboxamide (0.418 mmol) and DMF (10 mL), $Cs_2CO_3$ (0.31 mmol) and then add the diaryldisulfide (0.65 mmol). Heat the reaction under a nitrogen atmosphere at 100° C. for approximately 2.5 h (monitor by tlc/LC-MS to determine when the reaction is complete). Cool to rt, concentrate to a minimum volume and partition between brine and EtOAc (3 mL). Extract again with EtOAc, dry the combined extracts ($MgSO_4$), filter and concentrate the filtrate to provide the crude 3-arylthioindole-2-carboxamide. Purify the crude product on an ISCO (4.0 g $SiO_2$) column to provide the 3-arylthioindole-2-carboxamide I.

General Synthetic Procedure VIIc (Scheme 1, Optional Step f)

Treat a solution of the 3-arylthioindole-2-carboxamide (1 mmol) and with $H_2O_2$ (30% w/w, 2.5 mmol) and $Na_2CO_3$ (2.0 mmol). Stir at rt for 16 hours, quench with water, extract with EtOAc, wash with brine, dry ($MgSO_4$), filter and concentrate to afford the 3-arylsulfonyl-1H-indole-2-carboxylic acid amide I.

1H-indole-2-carboxylic acid amide 4 (X=H)(from the ethyl ester)

Treat ethyl indole-2-carboxylate 1 (X=H, 2.0 g, 10.57 mmol) as described in General Synthetic Procedure II to afford the title compound (1.3 g, 76.9%) as an ivory-colored powder: mp 233-234.5° C.; $^1H$ NMR (DMSO-$d_6$) δ 11.53 (brs, 1H), 7.95 (brs, 1H), 7.60 (d, 1H, J=8.1 Hz), 7.42 (d, 1H, J=8.0 Hz), 7.36 (brs, 1H), 7.17 (t, 1H, J=8.1 Hz), 7.11 (s, 1H), 7.02 (t, 1H, J=8.1 Hz).

1H-indole-2-carboxylic acid amide 4 (X=H)(from the indole-2-carboxylic acid)

Treat 1H-indole-2-carboxylic acid 3 (X=H, 1.0 g, 6.2 mmol) as described in General Synthetic Procedure V to afford the title compound (854 mg, 86.0%) as a yellow powder: mp 233-234.5° C.; $^1$H NMR (DMSO-$d_6$) δ 11.53 (brs, 1H), 7.95 (brs, 1H), 7.60 (d, 1H, J=8.1 Hz), 7.42 (d, 1H, J=8.0 Hz), 7.36 (brs, 1H), 7.17 (t, 1H, J=8.1 Hz), 7.11 (s, 1H), 7.02 (t, 1H, J=8.1 Hz). Anal. Calcd. For $C_9H_8N_2O$: C, 67.50; H, 5.03; N, 17.50. Found: C, 67.20; H, 4.95; N, 17.25.

3-Benzensulfonyl-5-chloro-1H-indole-2-carboxylic acid amide (Ia)

Treat 3-phenylsulfanyl-5-chloro-1H-indole-2-carboxylic acid amide (303 mg, 1.0 mmol) with $H_2O_2$ as described in General Synthetic Procedure VIIc to give Ia (Table 1) as a white solid; MS Obs 336 (M+1).

3-Benzensulfonyl-1H-indole-2-carboxylic acid amide (Ib)

Treat 3-phenylsulfanyl-1H-indole-2-carboxylic acid amide, (Ic. 268 mg, 1.0 mmol) with $H_2O_2$ as described in General Synthetic Procedure VIIc to give Ib as a white solid: mp 204° C. (dec); $^1$H NMR (DMSO-$d_6$) δ 12.9 (brs, 1H), 8.5 (brs, 1H), 8.2 (brs, 1H), 8.0 (m, 3H), 7.6 (m, 4H), 7.3 (m, 2H); MS Obs 301.1 (M+1); LC/MS: m/z=301 (M+H).

3-Phenylsulfanyl-1H-indole-2-carboxylic acid amide (Ic)

Treat 1H-indole-2-carboxylic acid amide 4 (X=H, 320 mg, 2.0 mmol) with phenyldisulfide (1.0 equiv., 436 mg), as described in General Synthetic Procedure VIIa, to afford the title compound (500 mg, 93.3%) as an ivory-colored solid, mp 197-197.5° C. Anal. Calcd. For $C_{15}H_{12}N_2SO$: C, 67.15; H, 4.51; N, 10.44. Found: C, 66.03; H, 4.42; N, 10.18.

5-Bromo-3-phenylsulfanyl-1H-indole-2-carboxylic acid amide (Id)

Treat 5-bromo-1H-indole-2-carboxylic acid ethyl ester 1 (X=Br, 4.67 mmol) with 7 N $NH_3$/MeOH as described in General Synthetic Procedure III to afford 5-bromo-1H-indole-2-carboxylic acid amide 4 (X=Br, $R^2$=$R^3$=H) as an ivory-colored solid. Treat 5-bromo-1H-indole-2-carboxylic acid amide (100 mg, 0.41 mmol) with diphenyldisulfide (1.50 equiv., 141 mg, 0.65 mmol) as described in General Synthetic Procedure VIIb to give the title compound Id (85 mg) as an ivory-colored solid. $^1$H NMR (DMSO-$d_6$) δ 12.5 (brs, 1H), 8.0 (brs, 1H), 7.72 (brs, 1H), 7.59-7.08 (m, 8H); LC/MS: m/z obs=347 (M+1).

3-(2-Amino-phenylsulfanyl)-5-methoxy-1H-indole-2-carboxylic acid amide (Ie)

Treat 5-methoxy-1H-indole-2-carboxylic acid 1 (X=$OCH_3$, 1.09 g, 5.71 mmol) as described in General Synthetic Procedure V to afford 5-methoxy-1H-indole-2-carboxylic acid amide 4 (X=$OCH_3$, $R^2$=$R^3$=H; 536 mg, 49%) as yellow solid, mp 204-205° C.; $^1$H NMR (DMSO-$d_6$) δ 11.3 (brs, 1H), 7.9 (brs, 1H), 7.3 (d, 2H), 7.1 (d, 2H), 6.8 (d, 1H). 3.8 (s, 3H); LC/MS: m/z obs=191 (M+1). Treat 5-methoxy-1H-indole-2-carboxylic acid amide (300 mg, 1.6 mmol) with 2-aminophenyldisulfide (1.4 equiv., 546 mg, 2.2 mmol) as described in General Synthetic Procedure VIIa to afford the title compound Ie (321 mg, 65%) as a light green solid, mp 203° C. (dec); $^1$H NMR (DMSO-$d_6$) δ 12.0 (brs, 1H), 8.0-7.8 (2brs, 2H), 7.4 (d, 1H), 7.1-6.9 (m, 4H), 6.8 (m, 1H). 6.6 (m, 1H), 5.5 (m, 2H), 3.8 (s, 3H); LC/MS: m/z obs=314 (M+1).

3-(3-Fluoro-phenylsulfanyl)-1H-indole-2-carboxylic acid amide (If)

Treat 1H-indole-2-carboxylic acid amide 4 (X=$R^2$=$R^3$=H; 225 mg, 1.4 mmol) with bis-3-fluorophenyldisulfide (1.5 equiv., 534 mg, 2.1 mmol) as described in General Synthetic Procedure VIIa to afford the title compound If (322 mg, 80%) as a white solid: tlc (silica gel) $R_f$=0.1 (40% EtOAc/heptane).

3-(2-Amino-phenylsulfanyl)-5-bromo-1H-indole-2-carboxylic acid amide (Ig)

Treat 5-bromo-1H-indole-2-carboxylic acid amide 4 (X=Br, $R^2$=$R^3$=H; 100 mg, 0.418 mmol) with 2-aminophenyldisulfide (1.5 equiv., 161 mg, 0.65 mmol) as described in General Synthetic Procedure VIIb to afford the title compound Ig (113 mg) as an ivory-colored solid. $^1$H NMR (DMSO-$d_6$) δ 12.25 (brs, 1H), 8.01 (brs, 1H), 7.9 (brs, 1H), 7.7 (s, 1H), 7.25-6.2 (m, 6H), 5.45 (s, 2H); LC/MS: m/z obs=361.99 (M+1).

3-(2-Amino-phenylsulfanyl)-1H-indole-2-carboxylic acid amide (Ih)

Treat 1H-indole-2-carboxylic acid amide 4 (X=$R^2$=$R^3$=H; 160 mg, 1.0 mmol) with 2-aminophenyldisulfide (1.4 equiv., 347 mg, 1.4 mmol) as described in General Synthetic Procedure VIIa to afford the title compound Ih (135 mg, 37%) as a light green solid: $^1$H NMR (DMSO-$d_6$) δ 12.1 (brs, 1H), 8.0 (brs, 1H), 7.88 (brs, 1H), 7.58 (d, 1H, J=7.8 Hz), 7.48 (d, 1H, J=8.7 Hz), 7.28-7.23 (m, 1H), 7.12-7.10 (m, 1H), 6.92-6.86 (m, 2H), 6.70-6.67 (m, 1H), 6.44-6.39 (m, 1H), 5.45 (brs, 2H); m/z obs=284 (M+1).

3-(Pyridin-2-ylsulfanyl)-1H-indole-2-carboxylic acid amide (Ii)

Treat 1H-indole-2-carboxylic acid amide 4 (X=$R^2$=$R^3$=H; 80.0 mg, 0.5 mmol) with 2,2'-dithiopyridine (1.0 equiv., 0.5 mmol) as described in General Synthetic Procedure VIIa to give the title compound Ii (71.0 mg, 53%) as a tan solid: MS Obs. 270.2 (M+1).

3-Phenylsulfanyl-1H-indole-2-carboxylic Acid Methylamide (Ij)

To a solution of 1H-indole-2-carboxylic acid 3 (X=H, 1.0 g, 6.21 mmol) and anhydrous THF (50 ml), add carbonyldiimidazole (1.10 equiv., 1.1 g, 6.83 mmol). Stir for 30 min at rt and then add $MeNH_2HCl$ (1.30 equiv., 541 mg, 8.07 mmol) in one portion. Add DMF (10 mL) to the reaction and stir at rt. After 2 h, pour the clear yellow reaction solution into $H_2O$. Collect the precipitate by filtration and dry under vacuum at 40° C. to afford 1H-indole-2-carboxylic acid methylamide 4 (X=$R^2$=H, $R^3$=$CH_3$; 860 mg, 80%) as a yellow solid, mp 222-223° C.; $^1$H NMR (DMSO-$d_6$) δ 11.6 (brs, 1H), 8.45 (m, 1H), 7.60 (d, 1H, J=7.8 Hz), 7.44 (dd, 1H, J=1.05, 8.25 Hz), 7.20-7.14 (m, 1H), 7.60-7.00 (m, 1H), 2.82 (d, 3H, J=4.2 Hz). m/z obs=175 (M+1). Treat 1H-indole-2-carboxylic acid methylamide (174 mg, 1.0 mmol) with phenyldisulfide (1.1 equiv., 240 mg, 1.1 mmol) as described in General Synthetic Procedure VIIa to afford the title compound Ij (140 mg, 50%) as an ivory-colored solid, mp 201-204° C.; $^1$H NMR (DMSO-$d_6$) δ 12.3 (brs, 1H), 8.3 (m, 1H), 7.48 (d, 1H), 7.42 (d, 1H), 7.3-7.0 (m, 7H), 2.9 (d, 3H).

3-(Pyridin-2-ylsulfanyl)-1H-indole-2-carboxylic acid methylamide (Ik)

Treat 1H-indole-2-carboxylic acid methylamide 4 (X=$R^2$=H, $R^3$=$CH_3$; 87 mg, 0.5 mmol) with 2,2'-dithiopyridine (1.3 equiv., 143 mg) as described in General Synthetic Procedure VIIa to afford the title compound Ik (93 mg, 66%) as a white solid: $^1$H NMR (DMSO-$d_6$) δ 12.3 (brs, 1H), 8.4 (m, 1H), 8.3 (m, 1H), 7.6 (m, 2H), 7.4 (m, 1H), 7.3 (m, 1H), 7.2 (m, 2H), 6.7 (d, 1H), 2.9 (d, 3H); MS obs 362 (M+1).

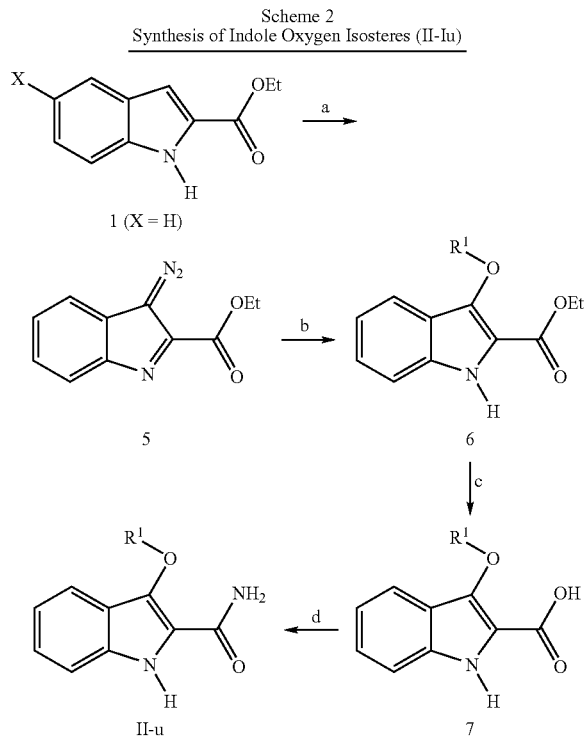

Scheme 2
Synthesis of Indole Oxygen Isosteres (II-Iu)

a) NaNO₂, HOAc, CH₂Cl₂, rt. b) R¹OH, Rh₂(OAc)₄, ClCH₂CH₂Cl, c) KOH, EtOH/H₂O d) Im₂CO, THF, NH₄OH.

3-Diazo-3H-indole-2-carboxylic acid ethyl ester (5) (Scheme 2, Step a)

Add glacial acetic acid (6 mL) dropwise with stirring at rt over 5 min to a solution of indole-2-carboxylic acid ethyl ester (1, X=H, 2.0 g, 10.6 mmol), and sodium nitrite (7.3 g, 106 mmol, 10 equiv.) under $N_2$ in $CH_2Cl_2$ (20 mL). After approximately 10 min., add $CH_2Cl_2$ (100 mL) to facilitate stirring the resultant suspension. Quench the reaction after 1.5 h with $H_2O$, remove the organic layer, and extract the aqueous phase with $CH_2Cl_2$. Wash the combined organic phases successively with saturated $NaHCO_3$ and brine, dry ($MgSO_4$), filter and concentrate to give, after purification, 5 (1.62 g, 71%) as a yellow solid. (Kettle et al. Tetrahedron Lett. 2000, 6905-6907).

General Synthetic Procedure VIII (for the Reaction of Diazo Compound 5 with Alcohols to Provide Indole Ethyl Esters 6; Scheme 2, Step b)

React 3-diazo-3H-indole-2-carboxylic acid ethyl ester 5 (0.9 mmol) with the desired aryl or alkyl alcohol (1.5 mmol) in 1,2-dichloroethane (10 mL) and a catalytic amount of $Rh_2(OAc)_4$ (0.08 equiv., 0.072 mmol, 32 mg), and heat at 85° C. for 3 h. Dilute the reaction mixture with $CH_2Cl_2$, filter through Celite® (diatomaceous earth) and concentrate to give the crude product. Purify the material by flash chromatography to afford the desired indole oxygen isosteres 6 as the ethyl esters.

General Synthetic Procedure IX (Hydrolysis of Ethyl 2-indole Carboxylates 6l-u to Carboxylic Acids 7l-u; Scheme II, Step c)

Add to a suspension of indole-2-carboxylic acid ethyl ester 6 (0.50 mmol) in EtOH (10 mL) a solution of KOH (5.0 equiv., 2.5 mmol, 140 mg) and $H_2O$ (2.0 mL). Stir at rt for 16 h, acidify (HCl) to pH 1 and collect the precipitate by filtration to afford the corresponding carboxylic acid 7.

3-Phenoxy-1H-indole-2-carboxylic acid amide (Il)

React 3-diazo-3H-indole-2-carboxylic acid ethyl ester, 5, (300 mg, 1.38 mmol) with phenol (5.0 equiv., 650 mg, 6.90 mmol) as described in General Synthetic Procedure VIII. Purify by flash chromatography to afford 3-phenoxy-1H-indole-2-carboxylic acid ethyl ester 6 ($R^1$=phenyl, 303 mg, 78%) as a yellow solid. Hydrolyze the ester to the carboxylic acid 7 ($R^1$=phenyl) using General Synthetic Procedure IX and then transform the carboxylic acid to the corresponding primary amide as described in General Synthetic Procedure V to afford the title compound Il as a light purple solid, tlc (silica gel) $R_f$=0.15.

3-(4-Methoxy-phenoxy-1H-indole-2-carboxylic acid amide (Im)

React 3-diazo-3H-indole-2-carboxylic acid ethyl ester, 5, (231 mg, 1.10 mmol) with 4-methoxyphenol (1.4 equiv., 186 mg, 1.5 mmol) as described in General Synthetic Procedure VIII to afford 3-(4-methoxyphenoxy-1H-indole-2-carboxylic acid ethyl ester 6 ($R^1$=4-methoxyphenyl, 169 mg, 51%) as an ivory-colored solid. Hydrolyze the ester to the carboxylic acid 7 ($R^1$=4-methoxyphenyl) using General Synthetic Procedure IX and then transform the carboxylic acid to the corresponding primary amide as described in General Synthetic Procedure V to afford the title compound Im as a colorless oil, tlc (silica gel) $R_f$=0.10.

3-(4-Fluoro-phenoxy-1H-indole-2-carboxylic acid amide (In)

React 3-diazo-3H-indole-2-carboxylic acid ethyl ester, 5, (220 mg, 1.0 mmol) with 4-fluorophenol (10.0 equiv., 1.1 g, 10.0 mmol) as described in General Synthetic Procedure VIII to afford 3-(4-fluoro-phenoxy-1H-indole-2-carboxylic acid ethyl ester 6 ($R^1$=4-fluorophenyl, 184 mg) as a white solid. Hydrolyze the ester to the carboxylic acid 7 ($R^1$=4-fluorophenyl) using General Synthetic Procedure IX and then transform the carboxylic acid to the corresponding primary amide as described in General Synthetic Procedure V to afford the title compound In as a white solid (109 mg), tlc (silica gel) $R_f$=0.40.

3-(2-Fluoro-phenoxy-1H-indole-2-carboxylic acid amide (Io)

React 3-diazo-3H-indole-2-carboxylic acid ethyl ester, 5, (220 mg, 1.0 mmol) with 2-fluorophenol (10.0 equiv., 1.1 g, 10.0 mmol) as described in General Synthetic Procedure VIII to afford 3-(2-fluoro-phenoxy-1H-indole-2-carboxylic acid ethyl ester 6 ($R^1$=2-fluorophenyl, 100 mg) as an ivory-colored solid. Hydrolyze the ester to the carboxylic acid 7 ($R^1$=2-fluorophenyl) using General Synthetic Procedure IX and then transform the carboxylic acid to the corresponding primary amide as described in General Synthetic Procedure V to afford the title compound Io as a white solid (59 mg), tlc (silica gel) Rf=0.07.

3-(4-Chloro-phenoxy-1H-indole-2-carboxylic acid amide (Ip)

React 3-diazo-3H-indole-2-carboxylic acid ethyl ester, 5, (220 mg, 1.0 mmol) with 4-chlorophenol (10.0 equiv., 1.3 g, 10.0 mmol) as described in General Synthetic Procedure VIII to afford 3-(4-chloro-phenoxy-1H-indole-2-carboxylic acid ethyl ester 6 ($R^1$=4-chlorophenyl, 90 mg) as a white solid. Hydrolyze the ester to the carboxylic acid 7 ($R^1$=4-chlorophenyl) using General Synthetic Procedure IX and then transform the carboxylic acid to the corresponding primary amide as described in General Synthetic Procedure V to afford the title compound Ip as an ivory-colored solid (50 mg), tlc (silica gel) Rf=0.09.

3-Methoxy-1H-indole-2-carboxylic acid amide (Iq)

React 3-diazo-3H-indole-2-carboxylic acid ethyl ester, 5, (300 mg, 1.38 mmol) with methanol (5.0 equiv., 0.3 mL, 6.91 mmol) as described in General Synthetic Procedure VIII to afford 3-methoxy-1H-indole-2-carboxylic Acid Ethyl Ester 6 ($R^1$=methyl, 210 mg) as a white solid [tlc (silica gel), Rf=0.50]. Hydrolyze the ester to the carboxylic acid 7 ($R^1$=methyl) using General Synthetic Procedure IX and then transform the carboxylic acid to the corresponding primary amide as described in General Synthetic Procedure V to afford the title compound Iq as a tan solid (40 mg), tlc (silica gel) Rf=0.03.

3-Ethoxy-1H-indole-2-carboxylic acid amide (Ir)

React 3-diazo-3H-indole-2-carboxylic acid ethyl ester, 5, (300 mg, 1.38 mmol) with ethanol (5.0 equiv., 0.4 mL, 6.90 mmol) as described in General Synthetic Procedure VIII to afford 3-ethoxy-1H-indole-2-carboxylic acid ethyl ester 6 ($R^1$=ethyl) as a white solid. Hydrolyze the ester to the carboxylic acid 7 ($R^1$=ethyl) using General Synthetic Procedure IX and then transform the carboxylic acid to the corresponding primary amide as described in General Synthetic Procedure V to afford the title compound Ir as a tan solid (124 mg), tlc (silica gel) Rf=0.07.

3-Isopropoxy-1H-indole-2-carboxylic acid amide (Is)

React 3-diazo-3H-indole-2-carboxylic acid ethyl ester, 5, (300 mg, 1.38 mmol) with isopropanol (5.0 equiv., 0.53 mg, 6.90 mmol) as described in General Synthetic Procedure VIII to afford 3-isopropoxy-1H-indole-2-carboxylic acid ethyl ester 6 ($R^1$=isopropyl) as a white solid (33 mg); tlc (silica gel) Rf=0.45. Hydrolyze the ester to the carboxylic acid 7 ($R^1$=isopropyl) using General Synthetic Procedure IX and then transform the carboxylic acid to the corresponding primary amide as described in General Synthetic Procedure V to afford the title compound Is as a tan solid (126 mg), tlc (silica gel)Rf=0.10.

3-tert-Butoxy-1H-indole-2-carboxylic acid amide (It)

React 3-diazo-3H-indole-2-carboxylic acid ethyl ester, 5, (220 mg, 1.0 mmol) with t-BuOH (10.0 equiv., 0.95 mL, 10.0 mmol) as described in General Synthetic Procedure VIII to afford 3-t-butoxy-1H-indole-2-carboxylic acid ethyl ester 6 ($R^1$=tert-butyl, 149 mg) as a white solid. Hydrolyze the ester to the carboxylic acid 7 ($R^1$=tert-butyl) using General Synthetic Procedure IX and then transform the carboxylic acid to the corresponding primary amide as described in General Synthetic Procedure V to afford the title compound It as a light green solid (39 mg), tlc (silica gel) Rf=0.09.

3-Benzyloxy-1H-indole-2-carboxylic acid amide (Iu)

React 3-diazo-3H-indole-2-carboxylic acid ethyl ester, 5, (305 mg, 1.4 mmol) with benzyl alcohol (5.0 equiv., 0.73 mL, 7.05 mmol) as described in General Synthetic Procedure VIII to afford 3-benzyloxy-1H-indole-2-carboxylic acid ethyl ester 6 ($R^1$=benzyl) as a white solid [MS obs=296 (M+1)]. Hydrolyze the ester to the carboxylic acid 7 ($R^1$=benzyl) using General Synthetic Procedure IX and then transform the carboxylic acid to the corresponding primary amide as described in General Synthetic Procedure V to afford the title compound Iu as a tan solid (115 mg), tlc (silica gel) Rf=0.1.

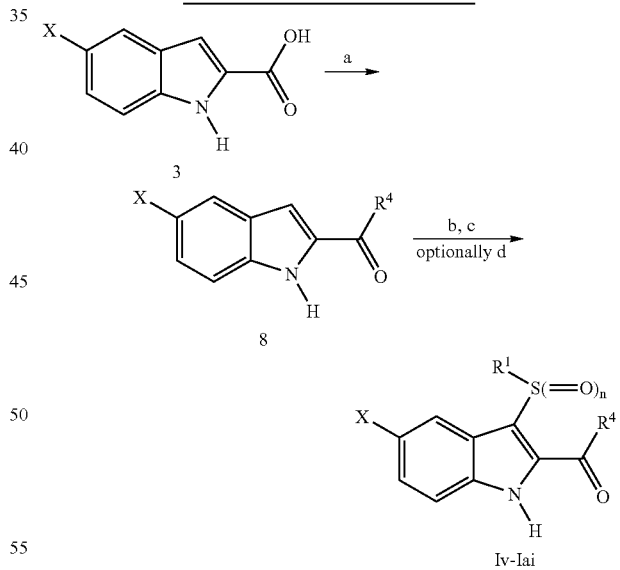

Scheme 3
Synthesis of Secondary Amides Iv-Iai $R^4$ = 4-morpholino, 1-piperidinyl, 1-pyrrolidinyl, 4-(tert-butoxycarbonyl)piperazin-1-yl or 4-piperazin-1-yl
a) carbonyldiimidazole/THF and morpholine, piperidine, pyrrolidine or N-(tert-butoxycarbonyl)piperazine; b) NaH/DMF/$R^1$—S—S—$R^1$;
c) $CF_3CO_2H$/HOAC to remove t-Boc protecting group when present; d) $H_2O_2$.

(3-Benzenesulfonyl-5-chloro-1H-indol-2yl)-morpholin-4-yl-methanone (Iv)

Treat 5-chloro-(1H-indol-2-yl)-morpholin-4-yl-methanone 8 (X=Cl, $R^4$=morpholin-4-yl) with phenyldisulfide as described in General Synthetic Procedure VIIa to give 3-phenylsulfanyl-5-chloro-1H-indol-2yl)-morpholin-4-yl-methanone. Treat 3-phenylsulfanyl-5-chloro-1H-indol-2yl)-morpholin-4-yl-methanone with $H_2O_2$ (30% w/v, 2.5 mmol) as described in General Synthetic Procedure VIIc to give the title compound Iv as a white solid.

(5-Fluoro-3-p-tolylsulfanyl-1H-indol-2-yl)-pyrrolidin-1-yl-methanone (Iw)

Treat 5-fluoro-1H-indole-2-carboxylic acid 3 (X=F, 516 mg, 3.0 mmol) with pyrrolidine (3.0 equiv., 0.76 mL, 9.0 mmol) as described in General Synthetic Procedure VIa to afford 5-fluoro-1H-indol-2yl-pyrrolidin-1-yl-methanone 8 (X=F, $R^4$=pyrrolidin-1-yl; 620 mg, 89%) as a white solid, mp 254-255° C. $^1$H NMR (DMSO-$d_6$) δ 11.7 (brs, 1H), 7.5-7.4 (m, 2H), 7.1 (td, 1H), 6.9 (s, 1H), 3.8 (t, 2H), 3.5 (t, 2H), 2.0-1.9 (m, 4H). Treat 5-fluoro-1H-indol-2yl-pyrrolidin-1-yl-methanone (327 mg, 2.0 mmol) with p-tolyldisulfide (450 mg, 2.6 mmol, 1.3 equiv.) as described in General Synthetic Procedure VIIa to afford the title compound Iw (334 mg, 47%) as a white amorphous solid: $^1$H NMR (DMSO-$d_6$) δ 12.2 (brs, 1H), 7.5 (m, 1H), 7.2-7.0 (m, 6H), 3.5 (m, 2H), 2.2 (s, 3H), 1.9-1.7 (m, 4H); m/z=355 (M+1).

(3-Phenylsulfanyl-1H-indol-2yl)-piperidin-1-yl-methanone (Ix)

Treat 1H-indole-2-carboxylic acid 3 (X=H, 750 mg, 4.66 mmol) with piperidine (3.0 equiv., 1.4 mL, 13.98 mmol) as described in General Synthetic Procedure VIa to afford 1H-indol-2yl-piperidin-1-yl-methanone 8 (X=H, $R^4$=piperidin-1-yl; 979 mg, 92%) as a white solid, mp 161-162° C. $^1$H NMR (DMSO-$d_6$) δ 11.5 (s, 1H), 7.6 (d, 1H), 7.4 (d, 1H), 7.2 (t, 1H), 7.1 (t, 1H), 6.7 (s, 1H), 3.7 (m, 4H), 1.7-1.5 (m, 6H). Treat 1H-indol-2yl-piperidin-1-yl-methanone (456 mg, 2.0 mmol) with phenyldisulfide (480 mg, 2.2 mmol) as described in General Synthetic Procedure VIIa to afford the title compound Ix (440 mg, 65%) as an opaque oil. $^1$H NMR (DMSO-$d_6$) δ 12.1 (brs, 1H), 7.5 (d, 1H), 7.4 (d, 1H), 7.3-7.1 (m, 3H), 7.1-7.0 (m, 4H), 6.7 (s, 1H), 3.6 (m, 2H), 3.4 (s, 8H), 3.2 (m, 2H), 1.8 (m, 4H), 1.4 (m, 2H). m/z=337 (M+1).

(5-Fluoro-3-phenylsulfanyl-1H-indol-2-yl)-pyrrolidin-1-yl-methanone (Iy)

Treat 5-fluoro-1H-indole-2-carboxylic acid 3 X=F, 516 mg, 3.0 mmol) with pyrrolidine (3.0 equiv., 0.76 mL, 9.0 mmol) as described in General Synthetic Procedure VIa to afford 5-fluoro-1H-indol-2yl-pyrrolidin-1-yl-methanone 8 (X=F, $R^4$=pyrrolidin-1-yl; 620 mg, 89%) as a white solid, mp 254-255° C. $^1$H NMR (DMSO-$d_6$) δ 11.7 (brs, 1H), 7.5-7.4 (m, 2H), 7.1 (td, 1H), 6.9 (s, 1H), 3.8 (t, 2H), 3.5 (t, 2H), 2.0-1.9 (m, 4H). Treat 5-fluoro-1H-indol-2-yl)-pyrrolidin-1-yl-methanone (200 mg, 0.86 mmol) with phenyldisulphide (1.5 equiv., 281 mg, 1.29 mmol) as described in General Synthetic Procedure VIIa to afford the title compound Iy (220 mg, 75%) as a pale yellow solid, mp 184-186° C. $^1$H NMR (DMSO-$d_6$) δ 12.3 (brs, 1H), 7.5 (m, 1H), 7.2 (m, 2H), 7.1-7.0 (m, 5H), 3.5 (m, 2H), 1.9-1.7 (m, 4H); m/z=341 (M+1).

[3-(2-Amino-phenylsulfanyl)-1H-indol-2-yl]-pyrrolidin-1-yl-methanone (Iz)

Treat 1H-indole-2-carboxylic acid 3 (X=H, 2.0 g, 12.4 mmol) with pyrrolidine (3.0 equiv., 3.1 mL, 37.2 mmol) as described in General Synthetic Procedure VIa to afford 1H-indol-2yl-pyrrolidin-1-yl-methanone 8 (X=H, $R^4$=pyrrolidin-1-yl; 2.46 g, 93%) as a white solid, mp 213-214° C. $^1$H NMR (DMSO-$d_6$) δ 11.5 (brs, 1H), 7.6 (d, 1H, J=8.1 Hz), 7.4 (d, 1H, J=8.1 Hz), 7.2 (m, 1H), 7.1 (m, 1H), 6.9 (m, 1H), 3.8 (m, 2H), 3.5 (m, 2H), 1.9-1.8 (m, 4H). Treat 1H-indol-2yl-pyrrolidin-1-yl-methanone (428 mg, 2.0 mmol) with 2-amino-phenyldisulphide (1.4 equiv., 694 mg, 2.8 mmol) as described in General Synthetic Procedure VIIa to afford the title compound Iz (468 mg, 69%) as a white solid. $^1$H NMR (DMSO-$d_6$) δ 11.9 (brs, 1H), 7.5 (d, 1H), 7.4 (d, 1H), 7.2 (m, 2H), 7.1 (m, 1H), 7.0 (m, 1H), 6.9 (d, 1H), 6.7 (m, 1H), 5.5 (brs, 2H), 3.5 (m, 2H), 1.9-1.7 (m, 4H); m/z=338 (M+1).

[3-(2-Amino-phenylsulfanyl)-1H-indol-2-yl]-pyrrolidin-1-yl-methanone Hydrochloride (Iaa)

Stir [3-(2-amino-phenylsulfanyl)-1H-indol-2-yl]-pyrrolidin-1-yl-methanone (Iz, 60 mg) in $Et_2O$ (5 mL) with 1N HCl (1 mL) and collect the precipitate by filtration. Wash the filter cake with $Et_2O$ and dry to afford the title compound Iaa (48 mg) as a white solid, mp 154-155° C.; m/z=338 (M+1)

[3-(2-Amino-phenylsulfanyl)-1H-indol-2-yl]-piperidin-1-yl-methanone (Iab)

Treat 1H-indole-2-carboxylic acid 3 (X=H, 750 mg, 4.66 mmol) with piperidine (3.0 equiv., 1.4 mL, 13.98 mmol) as described in General Synthetic Procedure VIa to afford 1H-indol-2yl-piperidin-1-yl-methanone 8 (X=H, $R^4$=piperidin-1-yl; 979 mg, 92%) as a white solid. Treat 1H-indol-2yl-piperidin-1-yl-methanone (116 mg, 0.51 mmol) with 2-aminophenyldisulfide (347 mg, 1.4 equiv.) as described in General Synthetic Procedure VIIa to afford the title compound Iab (103 mg, 29%) as a tan solid, m/z=352 (M+1).

[3-(2-Amino-phenylsulfanyl)-5-fluoro-1H-indol-2-yl]-piperidin-1-yl-methanone (Iac)

Treat 5-fluoro-1H-indole-2-carboxylic acid 3 (X=F, 1.7 g, 9.5 mmol) with piperidine as described in General Synthetic Procedure VIa to afford 5-fluoro-1H-indol-2yl-piperidin-1-yl-methanone 8 (X=F, $R^4$=piperidin-1-yl; 2.3 g, 100%) as a white solid. $^1$H NMR (DMSO-$d_6$) δ 11.7 (brs, 1H), 7.5-7.3 (m, 2H), 7.1-7.0 (m, 1H), 6.7 (s, 1H), 3.7 (m, 4H), 1.7-1.5 (m, 6H). Treat 5-fluoro-1H-indol-2yl-piperidin-1-yl-methanone (125 mg, 0.51 mmol) with 2-aminophenyldisulfide (347 mg, 1.4 equiv.) as described in General Synthetic Procedure VIIa to afford the title compound Iac (92 mg, 25%) as an ivory-colored solid, m/z=369 (M+1).

[5-Fluoro-3-(p-toluene-4-sulfinyl)-1H-indol-2-yl]-pyrrolidin-1-yl-methanone (Iad)

Treat 1w (100 mg, 0.28 mmol) with $H_2O_2$ (5 mL) in MeCN (5 mL) and $Na_2CO_3$ (50 mg) to afford the title compound Iad (10 mg) as a white solid. $^1$H NMR (DMSO-$d_6$) δ 12.4 (brs, 1H), 7.6 (d, 2H), 7.5 (m, 1H), 7.3 (d, 2H), 7.1-7.0 (m, 2H), 3.6-3.5 (m, 4H), 2.3 (s, 3H), 1.9 (m, 4H); m/z=371 (M+1).

(3-Phenylsulfanyl-1H-indol-2-yl)-piperazin-1-yl-methanone Hydrochloride (Iae)

Treat 1H-indole-2-carboxylic acid 3 (X=H, 1.0 mg, 6.21 mmol) with N-(tert-butoxycarbonyl)piperazine (1.10 equiv., 1.3 g, 6.83 mmol) as described in General Synthetic Procedure VIa to afford 4-(1H-indole-2-carbonyl)-piperazine-1-carboxylic acid tert-butyl ester 8 (X=H, R⁴=piperazin-4-yl-1-carboxylic acid tert-butyl ester; 2.0 g, 99%) as a white solid, mp 205-206° C. ¹H NMR (DMSO-d₆) δ 11.6 (brs, 1H), 7.6 (d, 1H), 7.4 (d, 1H), 7.2 (t, 1H), 7.1 (t, 1H0, 6.8 (s, 1H), 3.8-3.7 (m, 4H), 3.5-3.4 (m, 4H), 1.4 (s, 9H); m/z=330 (M+1). Treat 4-(1H-indole-2-carbonyl)-piperazine-1-carboxylic acid tert-butyl ester (329 g, 1.0 mmol) with phenyldisulfide (283 mg, 1.3 equiv., 1.3 mmol) as described in General Synthetic Procedure VIIa and then treat with trifluoroacetic acid (4 mL) in HOAc, to remove the Boc protecting group, to afford (3-phenylsulfanyl-1H-indol-2-yl)-piperazin-1-yl-methanone. Dissolve (3-phenylsulfanyl-1H-indol-2-yl)-piperazin-1-yl-methanone in EtOAc and treat with 1N HCl/Et₂O to provide the title compound Iae (103 mg, 29%) as a tan solid, mp 240° C. (dec); m/z=338 (M+1).

[5-Fluoro-3-(pyridin-2-ylsulfanyl)-1H-indol-2-yl]-pyrrolidin-1-yl-methanone (Iaf)

Treat 5-fluoro-1H-indole-2-carboxylic acid 3 (X=F, 516 mg, 3.0 mmol) with pyrrolidine (3.0 equiv., 0.76 mL, 9.0 mmol) as described in General Synthetic Procedure VIa to afford 5-fluoro-1H-indol-2yl-pyrrolidin-1-yl-methanone 8 (X=F, R⁴=pyrrolidin-1-yl; 620 mg, 89%) as a white solid, mp 254-255° C. ¹H NMR (DMSO-d₆) δ 11.7 (brs, 1H), 7.5-7.4 (m, 2H), 7.1 (td, 1H), 6.9 (s, 1H), 3.8 (t, 2H), 3.5 (t, 2H), 2.0-1.9 (m, 4H). Treat 5-fluoro-1H-indol-2yl-pyrrolidin-1-yl-methanone (464 mg, 2.0 mmol) with 2,2'-dithiopyridine (220 mg, 2.6 mmol, 1.3 equiv.) as described in General Synthetic Procedure VIIa to afford the title compound Iaf (258 mg, 38%) as a white solid: mp 204-206° C. ¹H NMR (DMSO-d₆) δ 12.2 (brs, 1H), 7.5 (m, 1H), 7.2-7.0 (m, 6H), 3.5 (m, 2H), 2.2 (s, 3H), 1.9-1.7 (m, 4H); m/z=355 (M+1).

[3-(Pyridin-2-ylsulfanyl)-1H-indol-2-yl]-pyrrolidin-1-yl-methanone (Iag)

Treat 1H-indole-2-carboxylic acid 3 (X=H, 2.0 g, 12.4 mmol) with pyrrolidine (3.0 equiv., 3.1 mL, 37.2 mmol) as described in General Synthetic Procedure VIa to afford 1H-indol-2yl-pyrrolidin-1-yl-methanone 8 (X=H, R⁴=pyrrolidin-1-yl; 2.46 g, 93%) as a white solid, mp 213-214° C. ¹H NMR (DMSO-d₆) δ 11.5 (brs, 1H), 7.6 (d, 1H, J=8.1 Hz), 7.4 (d, 1H, J=8.1 Hz), 7.2 (m, 1H), 7.1 (m, 1H), 6.9 (m, 1H), 3.8 (m, 2H), 3.5 (m, 2H), 1.9-1.8 (m, 4H). Treat 1H-indol-2yl-pyrrolidin-1-yl-methanone (214 mg, 1.0 mmol) with 2,2'-dithiopyridine (1.3 equiv., 286 mg, 1.3 mmol) as described in General Synthetic Procedure VIIa to afford the title compound Iag (200 mg, 69%) as a pale yellow solid, mp 211-213° C. ¹H NMR (DMSO-d₆) δ 12.3 (brs, 1H), 8.4 (m, 1H), 7.5 (m, 2H), 7.2-7.0 (m, 3H), 6.7 (d, 1H), 1.9-1.7 (m, 4H); m/z=342 (M+1).

Piperidin-1-yl-[3-(pyridin-2-ylsulfanyl)-1H-indol-2-yl]-methanone (Iah)

Treat 1H-indole-2-carboxylic acid 3 (X=H, 750 mg, 4.66 mmol) with piperidine (3.0 equiv., 1.4 mL, 13.98 mmol) as described in General Synthetic Procedure VIa to afford 1H-indol-2yl-piperidin-1-yl-methanone 8 (X=H, R⁴=piperidin-1-yl; 979 mg, 92%) as a white solid. Treat 1H-indol-2yl-piperidin-1-yl-methanone (114 mg, 0.50 mmol) with 2,2'-dithiopyridine (1.3 equiv., 143 mg) as described in General Synthetic Procedure VIIa to afford the title compound Iah (117 mg, 69%) as a pale yellow solid, m/z=338 (M+1).

[5-Fluoro-3-(pyridin-2-ylsulfanyl)-1H-indol-2-yl]-piperidin-1-yl-methanone (Iai)

Treat 5-fluoro-1H-indole-2-carboxylic acid 3 (X=F, 1.7 g, 9.5 mmol) with piperidine as described in General Synthetic Procedure VIa to afford 5-fluoro-1H-indol-2yl-piperidin-1-yl-methanone 8 (X=F, R⁴=piperidin-1-yl; 2.3 g, 100%) as a white solid. ¹H NMR (DMSO-d₆) δ 11.7 (brs, 1H), 7.5-7.3 (m, 2H), 7.1-7.0 (m, 1H), 6.7 (s, 1H), 3.7 (m, 4H), 1.7-1.5 (m, 6H). Treat 5-fluoro-1H-indol-2yl-piperidin-1-yl-methanone (123 mg, 0.50 mmol) with 2,2'-dithiopyridine (1.3 equiv., 143 mg) as described in General Synthetic Procedure VIIa to afford the title compound Iai (120 mg, 68%) as a yellow solid, m/z=356 (M+1).

TABLE 1

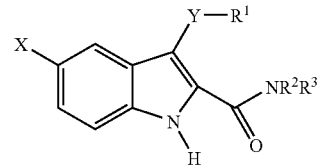

I

| Cmpd No. (Salt) | X | R¹ | NR²R³ | Y |
|---|---|---|---|---|
| Ia | 5-Cl | C₆H₅ | NH₂ | S(O)₂ |
| Ib | H | C₆H₅ | NH₂ | S(O)₂ |
| Ic | H | C₆H₅ | NH₂ | S |
| Id | 5-Br | C₆H₅ | NH₂ | S |
| Ie | 5-OCH₃ | 2-(NH₂)—C₆H₄ | NH₂ | S |
| If | H | 3-F—C₆H₄ | NH₂ | S |
| Ig | 5-Br | 2-(NH₂)—C₆H₄ | NH₂ | S |
| Ih | H | 2-(NH₂)—C₆H₄ | NH₂ | S |
| Ii | H | 2-pyridinyl | NH₂ | S |
| Ij | H | C₆H₅ | NHCH₃ | S |
| Ik | H | 2-pyridinyl | NHCH₃ | S |
| Il | H | C₆H₅ | NH₂ | O |
| Im | H | 4-(CH₃O)—C₆H₄ | NH₂ | O |
| In | H | 4-F—C₆H₄ | NH₂ | O |
| Io | H | 2-F—C₆H₄ | NH₂ | O |
| Ip | H | 4-Cl—C₆H₄ | NH₂ | O |
| Iq | H | CH₃ | NH₂ | O |
| Ir | H | C₂H₅ | NH₂ | O |
| Is | H | (CH₃)₂CH | NH₂ | O |
| It | H | (CH₃)₃C | NH₂ | O |
| Iu | H | C₆H₅CH₂ | NH₂ | O |

TABLE 2

Structure I:

Indole with X at 5-position, Y—R¹ at 3-position, C(=O)R⁴ at 2-position, NH

| Cmpd No. (Salt) | X | R¹ | R⁴ | Y |
|---|---|---|---|---|
| Iv | 5-Cl | $C_6H_5$ | —N(morpholino, with O) | $SO_2$ |
| Iw | 5-F | 4-$(CH_3)$—$C_6H_4$ | —N(pyrrolidinyl) | S |
| Ix | H | $C_6H_5$ | —N(piperidinyl) | S |
| Iy | 5-F | $C_6H_5$ | —N(pyrrolidinyl) | S |
| Iz | H | 2-$(NH_2)$—$C_6H_4$ | —N(pyrrolidinyl) | S |
| Iaa (HCl) | H | 2-$(NH_2)$—$C_6H_4$ | —N(pyrrolidinyl) | S |
| Iab | H | 2-$(NH_2)$—$C_6H_4$ | —N(piperidinyl) | S |
| Iac | 5-F | 2-$(NH_2)$—$C_6H_4$ | —N(piperidinyl) | S |
| Iad | 5-F | 4-$(CH_3)$—$C_6H_4$ | —N(piperidinyl) | SO |
| Iae (HCl) | H | $C_6H_5$ | —N(piperazinyl, NH) | S |
| Iaf | 5-F | 2-pyridinyl | —N(pyrrolidinyl) | S |
| Iag | H | 2-pyridinyl | —N(pyrrolidinyl) | S |
| Iah | H | 2-pyridinyl | —N(piperidinyl) | S |
| Iai | 5-F | 2-pyridinyl | —N(piperidinyl) | S |

Biological Methods

Casein Kinase Epsilon $^{33}$P-ATP Filter Plate Assay for Screening CK1ε Inhibitors Purpose: This assay measures the effect of compounds to inhibit the phosphorylation of the substrate casein by the enzyme casein kinase 1ε using an in vitro $^{33}$P-ATP filtration assay. Compounds are tested at five concentrations in duplicate in order to generate $IC_{50}$ values or % inhibition at a 10 micromolar concentration that are summarized in Table 4.

Materials:
  Equipment:
    Beckman Biomek 2000 Liquid Handling Robot
    Beckman Multimek 96 Automated 96 Channel Pipettor
    Millipore Vacuum Manifold Basic Kit # MAVM0960R
    Titertek Multidrop Liquid Dispenser
    Packard TopCount NXT Liquid Scintillation Counter
  Plates:
    Costar EIA/RIA Plate #9018
    Falcon 96 well U bottom Polystyrene Plate #353910
    Millipore Multiscreen 96 well Filtration Plates #MAPH-NOB50
    Millipore Multiscreen TopCount Adapter Plates #SE3M203V6
  Chemicals:
    EGTA from SIGMA #E-3889
    Casein (dephosphorylated) from SIGMA #C-4032
    ATP from SIGMA #A-7699
    DTT from Fisher Biotech #BP1725
    Trichloroacetic Acid from SIGMA #T-6399
    γ-$^{33}$P-ATP 1 mCi/37 MBq from Perkin Elmer Life Sciences #NEG-602H
  Enzyme:
    Casein Kinase 1ε final concentration 0.58 mg/ml obtained from fermentation and purification processes as are well known to one skilled in the art. The above are stored as 100 μL aliquots at minus 80° C.
  Compounds:
    Compounds for testing are supplied as frozen 10 mM compound stock dissolved in 100% DMSO.
  Assay Conditions:
    Final total assay volume per well is equal to 50 μL made up as follows:
    5 μL of diluted compound stock (10, 1, 0.1, 0.01 or 0.001 μM),
    5 μL of dephosphorylated casein final concentration 0.2 μg/μL,
    20 μL of CK1ε final concentration 3 ng/μL, and 20 μL of γ-$^{33}$P-ATP final concentration 0.02 μCi/μL mixed with cold ATP (10 μM final).

Methodology:
1. 500 mL of fresh assay buffer is made: 50 mM Tris pH 7.5, 10 mM MgCl$_2$, 2 mM DTT and 1 mM EGTA
2. Compounds to be evaluated are obtained as 10 μL of 10 mM stock dissolved in 100% DMSO. Using a Biomek 2000 liquid handling robot, serial dilutions are made to yield 10, 1, 0.1, 0.01 and 0.001 μM final compound dilutions added as 5 μL additions to Falcon U bottom plates. Typically 8 compounds are tested per 96 well plate with column 1 and 12 serving as control wells. A routine screening assay will consist of 32 compounds, which equals 4 assay plates.
3. Assay plate maps are set up according to the following pattern CK1ePlateMap.xls

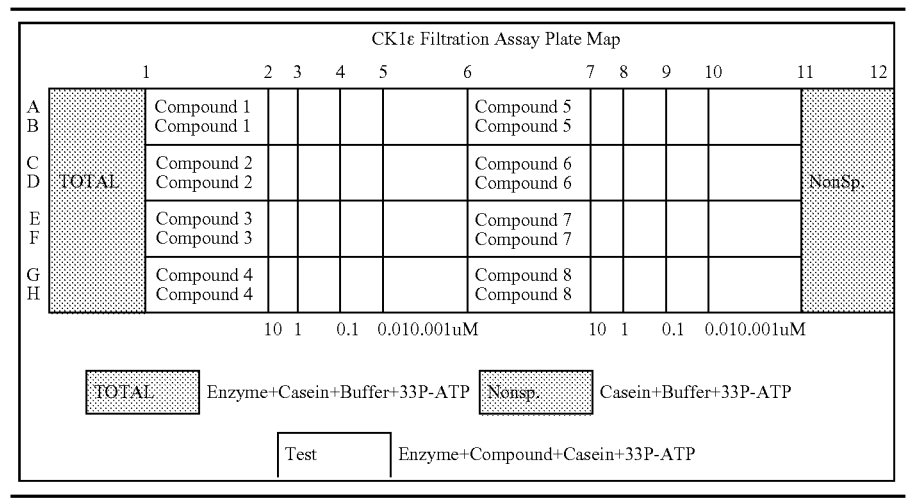

4. Once 5 μL of compound has been added as indicated, 5 μL of dephosphorylated casein (dissolved in distilled H$_2$O)(0.2 μg/μL) and 20 μL CK1ε (3 ng/μL) are added to the appropriate wells.
5. Finally 20 μL γ-$^{33}$P-ATP (0.02 μCi/μL)/10 μM cold ATP are added (equals approximately 2×10$^6$ CPM per well).
6. The Falcon U-Bottom assay plate containing the above 50 μL reaction volume is vortexed and then incubated at room temperature for 2 hours.
7. At the end of 2 hours, the reaction is stopped by the addition of 65 μL of ice cold 2 mM cold ATP (made up in assay buffer) to the assay plates using a Beckman Multimek
8. At the same time 25 μL 100% ice cold TCA made up in distilled H$_2$O is added to a matching number of Millipore MAPH filter plates.
9. Using a handheld 8-channel pipettor, 100 μL of the reaction mixture is transferred from the Falcon U-Bottom Plate to the Millipore MAPH filter plates presoaked with TCA.
10. The Millipore MAPH filter plates are mixed gently and allowed to sit at room temperature for at least 30 minutes to precipitate the proteins.
11. After 30 minutes the filter plates are placed on a Millipore vacuum manifold and filtered at no more than 8 mm Hg as the MAPH filters tend to "air lock" at higher vacuum settings.
12. The filter plates are sequentially washed and filtered with 2×150 μL 20% TCA, 2×150 μL 10% TCA and 2×150 μL 5% TCA (total of 6 washes per plate/900 μL per well).
13. Plates are allowed to dry overnight at room temperature. The next day 40 μL Packard Microscint-20 Scintillation Fluid is added per well using a Titertek Multidrop dispenser; the plates are sealed and counted for 2 minutes/well in a Packard Topcount NXT Scintillation Counter (CPM values/well are captured).

Calculation:
1. Counts Per Minute (CPM) data is captured and imported into a proprietary data calculation and archiving database (Activity Base by IDBS version 5.0).
2. Column 1 for each plate reflects total phosphorylation activity of the enzyme in the absence of any inhibiting compound and thus represents 100%. Column 12 reflects any nonspecific phosphorylation/retained radioactivity activity in the absence of inhibiting compound and enzyme. Typically we see approximately 1% of Total CPMs that are "nonspecific".
3. By having determined the "total" and "nonspecific" CPMs for each plate one is able to determine the % inhibition of the enzyme's ability to phosphorylate the substrate for each concentration of test compound. This % inhibition data is used to calculate an IC$_{50}$ value (concentration at which a compound is able to inhibit the enzyme activity by 50%) for a compound using a non-linear curve fit program contained with the Activitybase calculation protocol (DG0027-CK1-D-BL) (Study: RESR0290).
4. Kinetic studies have determined the K$_m$ value for ATP to be 21 μM in this assay system.

Casein Kinase 1δ Streptavidin Affinity Membrane Plate Assay for CKIδ inhibitors Purpose: To evaluate test compounds for CKIδ activity in Streptavidin Affinity Membrane (SAM) Biotin Capture Plate (Promega V7542)

Supplies and Reagents

HEPES Sigma # H3375 MW=238.3; β-Glycerol phosphate Sigma # G-9891 MW=216.0; EDTA 0.5M, pH 8.0 Gibco-BRL; Sodium orthovanadate ACROS # 205330500 MW=183.9; DTT (DL-dithiothreitol) Sigma # D-5545 MW=154.2; Magnesium Chloride ACROS # 41341-5000 MW=203.3; ATP Sigma # A-7699 MW=551.1; γ$^{33}$P ATP NEN # NEG602H; Casein Kinase 1δ Sigma # C4455; Casein Kinase 1 substrate New England Peptide Biotin-RRKDLH-DDEEDEAMSITA MW=2470
Prepare Kinase Buffer (KB, 100 mL) as follows:

| | |
|---|---|
| 50 mM HEPES, pH 8.0 | 5 mL of 1M stock |
| 10 mM MgCl | 1 mL of 1M stock |
| 10 mM β-glycerophosphate | 1 mL of 1M stock |
| 2.5 mM EDTA | 500 µL of 500 mM stock |
| 1 mM sodium orthovanadate | 100 µL of 1M stock |
| 1 mM DTT | 100 µL of 1 M stock |
| water | 92.3 mL |

Prepare ATP Master Mix as follows:
Prepare 1 mL of a 1M ATP solution in water (1M ATP stock).
To 12 mL kinase buffer (KB):
    Add 12 µl of 1M ATP solution, then
    Add 12 µl of $^{33}$P ATP (10 µCi/ul), NEG602H, Perkin Elmer
Prepare the reaction plate and conduct the assay as follows:
1. Add 10 µL of KB per well with or without the test compound inhibitor to reaction plate wells
2. Add 60 µL of KB per well
3. Add 10 µL of 500 µM Peptide Substrate per well
4. Bring plate up to 37° C.
5. Add 10 µL of 1:10 dilution of CK1δ per well=0.42 µg or 0.68 units
6. Initiate the reaction with 10 µL of ATP Master Mix per well
7. Place the reaction plate in 37° C. incubator for 10 min.
8. Stop the reaction with 10 µL of 1M ATP. Transfer 20 µL to the SAM Plate and let stand 10 min at room temperature.
9. Wash three times with 100 µL of 2M NaCl solution, then three times with 100 µL of 2M NaCl and 1% $H_3PO_4$ solutions and then three times with 100 µl of water on a vacuum manifold.
10. Dry the filter plate under a lamp for 30 min.
11. Seal bottom of plate and add 20 µL of MicroScint 20
12. Read in TOPCOUNT Cellular Circadian Assay Experimental Procedures Cell culture: Mper1-luc Rat-1 fibroblasts (P2C4) cultures were split every 3-4 days (~10-20% confluence) onto 150 cm² vented polystyrene tissue culture flasks (Falcon #35-5001) and maintained in growth media [EMEM (Cellgro #10-010-CV); 10% fetal bovine serum (FBS; Gibco #16000-044); and 50 I.U./mL penicillin-streptomycin (Cellgro #30-001-C1)] at 37° C. and 5% $CO_2$.
Stable transfection: Rat-1 fibroblast cultures at 30-50% confluence were co-transfected with vectors containing the Zeocin resistance selectable marker for stable transfection and an mPer-1 promoter-driven luciferase reporter gene. After 24-48 hours, cultures were split onto 96 well plates and maintained in growth media supplemented with 50-100 µg/mL Zeocin (Invitrogen #45-0430) for 10-14 days. Zeocin-resistant stable transfectants were assessed for reporter expression by supplementing growth media with 100 µM luciferin (Promega #E1603) and assaying luciferase activity on a TopCount scintillation counter (Packard Model #C384V00). Rat-1 clones expressing both Zeocin-resistance and mPer1-driven luciferase activity were synchronized by 50% horse serum [HS (Gibco #16050-122)] serum shock and assessed for circadian reporter activity. Mper1-luc Rat-1 fibroblasts clone P2C4 was selected for compound testing.
Synchronization protocol: Mper1-luc Rat-1 fibroblasts (P2C4) were plated (40-50% confluence) onto opaque 96-well tissue culture plates (PerkinElmer #6005680) and maintained in growth media supplemented with 100 µg/mL Zeocin (Invitrogen #45-0430) until cultures reached 100% confluence (48-72 h). Cultures were synchronized with 100 µL synchronization media [EMEM (Cellgro #10-010-CV); 100 I.U./mL penicillin-streptomycin (Cellgro #30-001-C1); 50% HS (Gibco #16050-122)] for 2 hours at 37° C. and 5% CO2. After synchronization, cultures were rinsed with 100 µL EMEM (Cellgro #10-010-CV) for 10 minutes at room temperature. After rinse, media was replaced with 300 µL CO2-independent media [CO2I (Gibco #18045-088); 2 mM L-glutamine (Cellgro #25-005-C1); 100 I.U./mL penicillin-streptomycin (Cellgro #30-001-C1); 100 µM luciferin (Promega #E1603)]. Compounds tested for circadian effects were added to $CO_2$-independent media in 0.3% DMSO (final concentration). Cultures were immediately sealed with TopSeal-A film (Packard #6005185) and transferred for luciferase activity measurement.
Automated Circadian Reporter Measurement: After synchronization, assay plates were maintained at 37° C. in a tissue culture incubator (Forma Scientific Model #3914). In Vivo luciferase activity was estimated by measuring relative light output on a TopCount scintillation counter (Packard Model #C384V00). Plates were transferred from incubator to reader using an ORCA robotic aim (Beckman Instruments) and SAMI-NT automated scheduling software (Version 3.3; SAGIAN/Beckman Instruments).
Data Analysis: Microsoft Excel and XLfit (Version 2.0.9; IDBS) were used to import, manipulate and graph data. Period analysis was performed either by determining the interval between relative light output minima over several days or by Fourier Transform. Both methods produced nearly identical period estimation over a range of circadian periods. Potency is reported as $EC_{\Delta\tau+1h}$, which is presented as the effective micromolar concentration that induced a 1 hour lengthening of period. The data was analyzed by fitting a hyperbolic curve to the data expressed as period change (y-axis) versus the concentration of test compound (x-axis) in XLfit and the $EC_{\Delta\tau+1h}$ was interpolated from this curve.

Rat Circadian Cycle Assay

This assay provides a means for assessing the effect of a test compound on circadian cycle in vivo. Use male Wistar rats (Charles River) with a starting body mass of 200-250 g. House each animal individually prior to testing in a controlled environment and maintain a thermoneutral ambient temperature of 24-28° C. under a 12/12 hour (h) light/dark cycle (lights on at 06:00 h), and give standard laboratory chow and water ad libitum. Implant each rat with an intra-abdominal biotelimetry transmitter (Minnimitter-VMFH, series 4000, Sunriver, Oreg.) to monitor core body temperature and general activity. Implant each transmitter as per the manufacturer's recommendations under ketamine/xylazine (78/13 mg $kg^{-1}$, ip) general anesthesia and allow the animals to recover for 7-10 days. After the recovery period, to establish each animal's internal circadian cycle, place the animals in a constant dark cycle (0/24 h light/dark cycle) and allow the animals to go into free run for 7-10 days prior to test compound administration. During the dosing regimen, animals receive either vehicle or compound (ip, sc, or po) at specific CTs (Circadian Times) over a 48 hour period. Monitor the animals for 5 to 7 days in a constant dark cycle (0/24 h light/dark cycle) after completion of the dosing regimen. For each experiment, sample abdominal temperature and general activity data at 5-minute intervals. For analysis, use the Vital-View and Actiview software supplied by Minimitter. Plot observed abdominal temperatures obtained for each rat on the first day on a horizontal line. Align the line of observed abdominal temperatures below an abscissa line with circadian time (x-axis). Plot observed abdominal temperatures for each successive day as individual lines in a similar manner to provide the ordinate (y-axis, in days). Connect the initial rise of core body temperature that occurs each day with a straight line, which allows the use of multiple days to estimate the circadian phase on any given day for each individual rat. Determine the effect of treatment on phase by using the straight line multi-day estimation of phase before and after dosing. Treatment with an active compound will cause a greater displacement between the straight line connecting the daily initial rise of core body temperature before compound treatment and the straight line connecting the initial rise of core body temperature after compound treatment versus the vehicle control before and after treatment lines. Calculate the difference between those phases projected onto the day prior to dosing for the treated animals. Use ANOVA, together with Students t test, to compare mean body temperature circadian shifts in minutes between groups.

TABLE 3

Biological Data*

| Cmpd No. | CKIε Inhibition IC$_{50}$ (μM) | Cell Assay EC$_{\Delta\tau+1h}$ (μM) |
|---|---|---|
| Ia | >10 | |
| Ib | 2.7 | |
| Ic | 3.1 | |
| Id | 0.42 | |
| Ie | 0.18 | >10 |
| If | 0.43 | 1.6 |
| Ig | 0.12* | 1.6 |
| Ih | 0.08* | |
| Ii | 187(n = 2) | |
| Ij | >10* | |
| Ik | >10* | |
| Il | >10* | |
| Im | 5.8 | |
| In | 0.89* | |
| Io | 2.4 | |
| Ip | 2.8 | |
| Iq | 13.5 | |
| Ir | 8.7 | |
| Is | 8.9 | |
| It | 11.7 | |
| Iu | 9.9 | |

*denotes average of two or more determinations;
compounds Iv-Iai: CKIε Inhibition IC$_{50}$ >10 μM

What is claimed is:

1. A method for inhibiting casein kinase Iε activity in a patient comprising the administration to said patient a therapeutically effective amount of a compound of formula I, or a stereoisomer, enantiomer, racemate, tautomer or a pharmaceutically acceptable salt thereof,

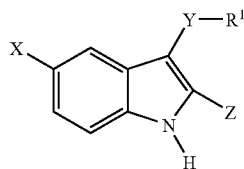

I wherein
X is H, Cl, F, Br, NO$_2$, CN, OR$^2$, NR$^2$R$^2$, HNSO$_2$—C$_{1-3}$alkyl, or NHCO—C$_{1-3}$alkyl;
Y is —S— or —O—;

R$^1$ is
1) aryl, unsubstituted or substituted with one or more:
   a) C$_{1-5}$alkoxy,
   b) OH,
   c) halogen,
   d) NR$^2$R$^2$,
   e) C$_{1-5}$alkyl, unsubstituted or substituted with one or more:
      i) OH or
      ii) C$_{1-5}$alkoxy;
2) a heterocycle, substituted or un-substituted with one or more:
   a) C$_{1-5}$alkyl, substituted or un-substituted with one or more:
      i) OH or
      ii) C$_{1-5}$alkoxy,
   b) C$_{1-5}$alkoxy,
   c) OH,
   d) halogen, or
   e) NR$^2$R$^2$;
3) C$_{1-5}$alkyl, substituted or un-substituted with one or more of:
   a) C$_{1-5}$alkyl,
   b) C$_{1-5}$alkoxy,
   c) OH, or
   d) aryl, substituted or un-substituted with one or more of:
      i) C$_{1-5}$alkyl,
      ii) C$_{1-5}$alkoxy,
      iii) OH,
      iv) halogen, or
      v) NR$^2$R$^2$;
Z is
   1) C(=O)NR$^2$R$^3$ or
   2) C(=O)R$^4$;
R$^2$ is hydrogen or C$_{1-3}$alkyl;
R$^3$ is hydrogen, C$_{1-5}$alkyl, or C$_{3-6}$cycloalkyl; and
R$^4$ is 1-piperidinyl, 1-pyrrolidinyl, 1-piperazinyl or 4-morpholinyl, unsubstituted or substituted with one or more of:
   1) C$_{1-5}$alkyl,
   2) C$_{1-5}$alkoxy,
   3) OH,
   4) halogen, or
   5) NR$^2$R$^2$.

2. The method as recited in claim 1 wherein the inhibition of casein kinase Iε activity results in altering of circadian rhythm period.

3. The method of claim 1 wherein
Y is S,
Z is C(=O)NHCH$_3$, and
R$^1$ is phenyl or pyridinyl.

4. The method of claim 3 wherein the compound is selected from the group consisting of:
3-phenylsulfanyl-1H-indole-2-carboxylic acid methylamide, and
3-(pyridin-2-ylsulfanyl)-1H-indole-2-carboxylic acid methylamide.

5. The method of claim 1 wherein
Y is O,
Z is C(=O)NH$_2$, and
R$^1$ is phenyl, substituted phenyl, C$_{1-5}$alkyl or substituted C$_{1-5}$alkyl.

6. The method of claim 5 wherein the compound is selected from the group consisting of:
- 3-phenoxy-1H-indole-2-carboxylic acid amide,
- 3-(4-methoxy-phenoxy)-1H-indole-2-carboxylic acid amide,
- 3-(4-fluoro-phenoxy)-1H-indole-2-carboxylic acid amide,
- 3-(2-fluoro-phenoxy)-1H-indole-2-carboxylic acid amide,
- 3-(4-chloro-phenoxy)-1H-indole-2-carboxylic acid amide,
- 3-methoxy-1H-indole-2-carboxylic acid amide,
- 3-ethoxy-1H-indole-2-carboxylic acid amide,
- 3-isopropoxy-1H-indole-2-carboxylic acid amide,
- 3-tert-butoxy-1H-indole-2-carboxylic acid amide, and
- 3-benzyloxy-1H-indole-2-carboxylic acid amide.

7. The method of claim 1 wherein:
Y is S,
Z is C(=O)$R^4$, and
$R^4$ is 1-piperidinyl, 1-pyrrolidinyl, 1-piperazinyl or 4-morpholinyl.

8. The method of claim 7 wherein the compound is selected from the group consisting of:
- (5-fluoro-3-p-tolylsulfanyl-1H-indol-2-yl)-pyrrolidin-1-yl-methanone,
- (3-phenylsulfanyl-1H-indol-2-yl)-piperidin-1-yl-methanone,
- (5-fluoro-3-phenylsulfanyl-1H-indol-2-yl)-pyrrolidin-1-yl-methanone,
- [3-(2-amino-phenylsulfanyl)-1H-indol-2-yl]-pyrrolidin-1-yl-methanone,
- [3-(2-amino-phenylsulfanyl)-1H-indol-2-yl]-piperidin-1-yl-methanone,
- [3-(2-amino-phenylsulfanyl)-5-fluoro-1H-indol-2-yl]-piperidin-1-yl-methanone,
- (3-phenylsulfanyl-1H-indol-2-yl)-piperazin-1-yl-methanone hydrochloride,
- [5-fluoro-3-(pyridin-2-ylsulfanyl)-1H-indol-2-yl]-pyrrolidin-1-yl-methanone,
- [3-(pyridin-2-ylsulfanyl)-1H-indol-2-yl]-pyrrolidin-1-yl-methanone, piperidin-1-yl-[3-(pyridin-2-ylsulfanyl)-1H-indol-2-yl]-methanone, and
- [5-fluoro-3-(pyridin-2-ylsulfanyl)-1H-indol-2-yl]-piperidin-1-yl-methanone.

9. The method of claim 1 wherein
Y is S,
Z is C(=O)$NH_2$, and
$R^1$ is pyridinyl.

10. The method of claim 9 wherein the compound is 3-(pyridin-2-ylsulfanyl)-1H-indole-2-carboxylic acid amide.

11. The method of claim 1 wherein
Y is S,
Z is C(=O)$NH_2$, and
$R^1$ is phenyl or substituted phenyl.

12. The method of claim 11 wherein the compound is selected from the group consisting of:
- 3-phenylsulfanyl-1H-indole-2-carboxylic acid amide,
- 5-bromo-3-phenylsulfanyl-1H-indole-2-carboxylic acid amide,
- 3-(2-amino-phenylsulfanyl)-5-methoxy-1H-indole-2-carboxylic acid amide,
- 3-(3-fluoro-phenylsulfanyl)-1H-indole-2-carboxylic acid amide,
- 3-(2-amino-phenylsulfanyl)-5-bromo-1H-indole-2-carboxylic acid amide, and
- 3-(2-amino-phenylsulfanyl)-1H-indole-2-carboxylic acid amide.

\* \* \* \* \*